US007829303B1

(12) United States Patent
Benson et al.

(10) Patent No.: US 7,829,303 B1
(45) Date of Patent: Nov. 9, 2010

(54) LIGAND SCREENING METHOD USING A CRYSTAL OF BETA SECRETASE

(75) Inventors: Timothy Earl Benson, Chesterfield, MO (US); Daisy Danielle Woods, South San Francisco, CA (US); Donald Bryan Prince, Norman, OK (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 12/206,421

(22) Filed: Sep. 8, 2008

Related U.S. Application Data

(63) Continuation of application No. 10/435,533, filed on May 9, 2003, now Pat. No. 7,442,537.

(60) Provisional application No. 60/379,690, filed on May 10, 2002.

(51) Int. Cl.
G01N 33/53 (2006.01)
G01N 31/00 (2006.01)
C12Q 1/37 (2006.01)
(52) U.S. Cl. .................. 435/23; 435/7.1; 702/27
(58) Field of Classification Search ................ None
See application file for complete search history.

(56) References Cited

U.S. PATENT DOCUMENTS

| 5,744,346 | A  | 4/1998  | Chrysler et al. |
| 5,942,400 | A  | 8/1999  | Anderson et al. |
| 6,221,645 | B1 | 4/2001  | Chrysler et al. |
| 6,225,103 | B1 | 5/2001  | Keolsch et al. |
| 6,245,884 | B1 | 6/2001  | Hook |
| 6,258,386 | B1 | 7/2001  | Xia et al. |
| 6,268,158 | B1 | 7/2001  | Pantoliano et al. |
| 6,291,223 | B1 | 9/2001  | Christie et al. |
| 6,297,021 | B1 | 10/2001 | Nienaber et al. |
| 6,329,163 | B1 | 12/2001 | Anderson et al. |
| 6,420,534 | B1 | 7/2002  | Gurney et al. |
| 6,440,698 | B1 | 8/2002  | Gurney et al. |
| 6,545,127 | B1 | 4/2003  | Tang et al. |
| 6,627,739 | B1 | 9/2003  | Anderson et al. |
| 7,217,556 | B1 | 5/2007  | Benson et al. |
| 7,384,773 | B1 | 6/2008  | Benson et al. |
| 7,442,537 | B1 | 10/2008 | Benson et al. |
| 7,524,668 | B1 | 4/2009  | Benson et al. |
| 7,601,528 | B1 | 10/2009 | Benson et al. |
| 2001/0016324 | A1 | 8/2001 | Gurney et al. |
| 2001/0018208 | A1 | 8/2001 | Gurney et al. |
| 2001/0021391 | A1 | 9/2001 | Gurney et al. |
| 2002/0037315 | A1 | 3/2002 | Gurney et al. |
| 2002/0049303 | A1 | 4/2002 | Tang et al. |
| 2002/0055459 | A1 | 5/2002 | Chopra et al. |
| 2002/0064819 | A1 | 5/2002 | Gurney et al. |
| 2002/0081634 | A1 | 6/2002 | Gurney et al. |
| 2002/0115600 | A1 | 8/2002 | Keolsch et al. |
| 2003/0095958 | A1 | 5/2003 | Bhisetti et al. |
| 2004/0014194 | A1 | 1/2004 | Beyer et al. |
| 2006/0136141 | A1 | 6/2006 | Benson et al. |
| 2008/0201123 | A1* | 8/2008 | Cosgrove ............... 703/11 |
| 2008/0215249 | A1 | 9/2008 | Benson et al. |
| 2009/0125259 | A1 | 5/2009 | Nicholls et al. |
| 2009/0170128 | A1 | 7/2009 | Benson et al. |

FOREIGN PATENT DOCUMENTS

| WO | WO 00/17369 | 3/2000 |
| WO | WO 01/00663 | 1/2001 |
| WO | WO 01/00665 | 1/2001 |
| WO | WO 01/49097 | 7/2001 |
| WO | WO 01/49098 | 7/2001 |
| WO | WO 01/50829 | 7/2001 |
| WO | WO 02/25276 | 3/2002 |
| WO | WO 01/23533 | 4/2002 |
| WO | WO 02/053594 | 7/2002 |
| WO | WO 03/012089 | 2/2003 |

OTHER PUBLICATIONS

McPherson et al., Eur. J. Biochem. 189:1-23, 1990.*
Kierzek et al., Biophys Chem 91:1-20, 2001.*
Nienaber et al., Nat. Biotechnol. 18:1105-1108, 2000.*
Alvares et al., "Rat urate oxidase produced by recombinant baculovirus expression: formation of peroxisome crystalloid core-like structures", Jun. 1992 Proceedings of the National Academy of Sciences USA vol. 89: pp. 4908-4912.
Dealwis et al., "X-ray analysis at 2.0 Angstrom resolution of mouse submaxillary rennin complexed with a decapeptide inhibitor CH-66, based on the 4- 16 fragment of rat angiotensinogen", Feb. 1994, Journal of Molecular Biology, vol. 236: pp. 342-360.
Giege et al., Crystallogenesis of Biological Macromolecules: Facts and Perspectives, Jul. 1994m /acta /crystallographic Section D., vol. 50:pp. 339-350.
Kervinen et al., "Toward a universal inhibitor of retroviral proteases: Comparative analysis of the interactions of LP-130 complexed with proteases from HIV-1, FIV and EIAV", Nov. 1998, Protein Science, Bol. 7: pp. 2314-2323.
Berman et al., "The Protein Data Bank," Nucleic Acids Res. Jan. 1, 2000:28(1): 235-42.
Bartlett et al., "CAVEAT: a program to facilitate the structure-derived design of biologically active molecules," Molecular Recognition: Chemical and Biological Problems, Royal Society of Chemistry, Special Pub No. 78:182-196 (1989).

(Continued)

Primary Examiner—David J Steadman
(74) Attorney, Agent, or Firm—McDonnell Boehnen Hulbert & Berghoff LLP

(57) ABSTRACT

The x-ray crystal structure of BACE or BACE-like proteins is useful for solving the structure of other molecules or molecular complexes, and identifying and/or designing potential modifiers of BACE activity.

9 Claims, 6 Drawing Sheets

OTHER PUBLICATIONS

Benson et al., "An enzyme-substrate complex involved in bacterial cell wall biosynthesis," National Struct. Biolo. 1995 (8):644-53.

Blundell et al., Protein Crystallography, Academic Press, New York, NY; title page, publication page, and table of contents only, 8 pages (1976).

Bohm, "The computer program LUDI: a new method for the de novo design of enzyme inhibitors," J Comput Aided Mol Des. 1992:6(1):61-78.

Branden et al., "introduction to protein structure," Garland Publishing, Inc., New York, NY 1999; Cover page, copyright page, and pp. 373-374.

Bruinzeel et al., "Recombinant insect cell expression and purification of human •-secretase (BACE-1) for X-ray crystallography," Protein Expr. Pruif. Oct. 2002: 26(1):139-148.

Ehehalt et al., "Splice variants of the •-site APP-cleaving enzyme BACE1 in human brain and pancreas," Biochem Biophys Res Commun. Apr. 26, 2002:293(1):30-37.

Drenth, "Principles of Protein X-ray Crystallograph," Second Edition, 1994 Springer-Verlag New York, Inc. pp. 1-18.

Brunger, "X-PLOR: Version 3.1, a System for X-Ray Crystallography and NMR", Yale University Press, New Haven & London, 1992; cover page, publication page and table of contents; 13 pages.

Brunger et al., "Slow-cooling protocols for crystallographic refinement by simulated annealing," Acta Crystallogr A. Jul. 1, 1990:46(Pt 7): 585-93.

Collaborative Computational Project, No. 4, "The CCP4 suite: programs for protein crystallography" Acta Cryst. 1994:D50:760-3.

CNX: Crystallograph and NMR eXplorer datasheet, Accelrys Corporate Headquarters, San Diego, CA (2001). [retrieved Aug. 30, 2002 from the Internet: URL:http://www.accelrys.com 2 pgs.].

Eisen et al., "HOOK:A program for finding novel molecular architectures that satisfy the chemical and steric requirements of a macromolecule binding site," Proteins. 1994;19(3):199-221.

Epps et al., "The ligand affinity of proteins measured by isothermal denaturation kinetics," Anal Biochem. May 1, 2001;292(1):40-50.

Hussain et al., "Identification of novel aspartic protease (Asp 2) as •-secretase," Mol Cell Neurosci. Dec. 1999;14(6):419-27.

Jiang et al, "Protein hydration observed by X-ray diffraction. Solvation properties of penicillopepsin and neuraminidase crystal structures," J Mol Biol. Oct. 14, 1994:243(1)100-15.

Kang et al., "The precursor of Alzheimer's disease amyloid a4 protein resembles a cell-surface receptor," Nature. Feb. 19, 1987;325(6106):733-6.

Kitaguchi et al., "Novel precursor of Alzheimer's disease amyloid protein shows protease inhibitory activity," Nature Feb. 11, 1988;331(6156):530-2.

Kuntz et al., "A geometric approach to macromolecule-ligand interactions," J Mol Biol. Oct. 25, 1982:161(2):269-88.

Lattman, "Use of the Rotation and Translation Functions," Meth. Enzymol. 1985;115:55-77.

Lauri et al., CAVVEAT: a program to facilitate the design of organic molecules, J. Comput. Aided Mol. Des 1994;8:51-66.

Lin et al., "Human aspartic protease memapsin 2 cleaves the •-secretase site of •-amyloid precursor protein," Proc Natl Acad Sci USA Feb. 15, 2000;97(4):1456-60.

Mallender et al., "Characterization of recombinant, soluble beta-secretase from an insect cell expression system," Mol Pharmacol Mar. 2001, 59(3):619-26.

Martin, "3D Database Searching in Drug Design," J. Med Chem 1992;35:2145-2154.

Meng et al., "Automated Docking with Grid-Based Energy Evaluation," J. Comp. Chem. 1992;13:505-524.

Miranker et al., "Functionality Maps of Binding Sites: A multiple Copy Simultaneous Search Method," Proteins: Struct. Funct. Gen. 1991;11:29-34.

National Institutes of Health, "BLAST 2 Sequences," [online} United States; retrieved Aug. 29, 2001 from the Internet: <URL:http://www.ncbi.nlm.nih.gov/gorf/bl2.html.> 1 pg.

Navaza, "AMoRe: an automated package for molecular replacement," Acta Cryst. 1994; A50:157-163.

Nishibata et al., "Automatic Creation of Drug Candidate Structures Based on Receptor Structure. Starting Point for Artificial Lead Generation," Tetrahedron. 1991;47:8985-90.

Noren et al., "A general method for site-specific incorporation of unnatural amino acids into protein," Science Apr. 14, 1989;244(4901):182-8.

Otwinowski, "Maximum Likelihood Refinement of Heavy Atom Parameters," Isomorphous Replacement and Anomalous Scattering, Wolf et al., eds., Science & Engineering Research Council, Daresbury Laboratory, Warrington, U>K., Proceedings of the CCP4 Study Weekend, Jan. 25-26, 1991; pp. 80-86.

Park et al., "Molecular Characterization of Candidate •-secretases, BACE1 and BACE2." ScholarOne, Inc. [online] Session No. 180.11; Society for Neuroscience's 30th Annual Meeting, New Orleans, LA, Nov. 4-9, 2001 [retrieved on Oct. 29, 2001]. Retrieved from the Internet URL:<hhtpL//sfn.scholarone.com/itin2000/main. html?new_page_id=76&abstract)id=19280&is_tech=0>, 1 page abstract.

Ponte et al., "A new A4 amyloid mRNA contains a domain homologous to serine proteinase inhibitors," Nature Feb. 11, 1988;331(6156):525-7.

Research Collaboratory for Structural Bioinformatics, "Protein Data Bank," [online] United States; retrieved Apr. 9, 2001 from the Internet: <URL:http:..www.rcsb.org/pdb/> 2 pages.

Research Collaboratory for Structural Bioinformatics, "Protein Data Bank," [online] United States; retrieved Aug. 30, 2002 from the Internet: <URL:http:..www.rcsb.org/pdb/> 8 pages.

Rossman, ed., The Molecular Replacement Method—A Collection of Papers on the Use of Non-Crystallographic Symmetry, Intl. Sci. Rev. Ser. No. 13, Gordon & Breach, New York, NY; title page, publication page, and table of contents only, 6 pages (1972).

Sack, "CHAIN-A Crystallographic Modeling Program," J. Mol. Graph 1988;6:224-25.

Sauder et al., "Modeling of substrate specificity of the Alzheimer's disease amyloid precursor protein beta-secretase," J. Mol Biol Jul. 7, 2000;300(2):241-8.

Shi et al., "The pro domain of •-secretase does not confer strict zymogen-like properties but does assist proper folding of the protease domain," J Biol Chem. Mar. 30, 2001;276(13):10366-73.

Sinha et al., "Purification and cloning of amyloid precursor protein •-secretase from human brain," Nature. Dec. 2, 1999;402(6761)537-40.

Skovronsky et al., "Beta-secretase revealed : starting gate for race to novel therapies for Alzheimer's disease," Trends Pharmacol Sci. May 2000;21(5):161-3.

Tanzi et al., "Protease inhibitor domain encoded by an amyloid protein precursor mRNA associated with Alzheimer's disease," Nature. Feb. 11, 1988; 331(6156): 528.30.

Tatusova et al., "BLAST 2 Sequences, a new tool for comparing protein and nucleotide sequences," FEMS Microbiol Lett. 1999;174:247-50 (program available at http://www.ncbinlm.nih.gov/gorf/b12.html).

Travis, "Proteins and organic solvents make an eye-opening mix," Science. 1993 No. 26;262(5138:1374.

Turner et al., "Substrate specificity of memapsin 2 (beta-secretase): Basis for inhibitor drug design for Alzheimer's disease," Experimental Biology 2001 Conference. Orlando, Florida, USA. Mar. 31-Apr. 4, 2001. Abstracts, part I. FASEB J. 2001 Nar 7;15(6):A538.

Van Duyne et al., "Atomic Structures of the Human Immunophilin FKBP-12 Complexes with FK506 and Rapamycin," J. Mol. Biol. 1993;229:105-24.

Vassar et al., "•-secretase cleavage of Alzheimer's amyloid precursor protein by the transmembrane aspartic protease BACE," Science. Oct. 22, 1999;286(5440):735-41.

Wyckoff et al., eds., Methods in Enzymology, vol. 114, Diffraction Methods for Biological Macromolecules, Academic Press, Orlando, FL, title page, publication page, and table of contents only, 5 pages total (1985).

Ermolieff et al., "Proteolytic activation of recombinant pro-memasin 2 (pro-beta-secretase) studied with new fluorogenic substrates," Biochemistry Oct. 10, 2000;39(40):12450-6.

Fairlie et al., "Conformational selection of inhibitors and substrates by proteolytic enzymes: implications for drug design and polypeptide processing," J Med Chem. Apr. 6, 2000;43(7):1271-81.

Farzan et al., "BACE2, a •-secretase homolog, cleaves at the • site and within the amyloid-• region of the amyloid-• precursor protein," Proc Natl Acad Sci USA Aug. 15, 2000;97(17):9712-9717.

Finzel, "LORE: Exploiting database of known structures," Meth. Enzymol. 1997;277(B):230-42.

Ghosh et al., "Structure-based design: Potent inhibitors of human brain memapsin 2 (•-secretase)," J Med Chem. Aug. 30, 2001:44(18):2865-2868.

Gillet et al., "SPROUT: a program for structure generation," J Comput Aided Mol Des. 1993(2):127-53.

Goodford, "A computational procedure for determining energetically favorable binding sites on biologically important macromolecules," J Med Chem Jul. 1985:28(7):849-57.

Goodsell et al., "Automated docking of substrates to proteins by simulated annealing," Proteins 1990;8(3)195-202.

Haniu et al., "Characterization of Alzheimer's beta -secretase protein BACE. A pepsin family member with unusual properties," J Biol Chem. Jul. 14, 2000;275(28):21099-106.

Hendrickson et al., "Selenomethionyl proteins produced for analysis by multiwavelength anomalous diffraction (MAD): a vehicle for direct determination of three-dimensional structure," EMBO J. 1990;9(5):1665-72.

Hong et al., "Structure of the protease domain of memapsin 2 (beta-secretase) complexed with inhibitor," Science. Oct. 2000 6L 290(5489)L150-3.

Huang et al,. "A 3D-structural model of memapsin 2 protease generated from theoretical study," Acta Pharmacol Sin. Jan. 2001:22(1):50-56.

Yan et al., (1999), "membrane-anchored aspartyl protease with Alzheimer's disease •-secretase activity," Nature. Dec. 2, 1999;402(6761):533-7.

McPherson et al., "The science of macromolecular crystallization," Aug. 1995, Structure, vol. 3, pp. 759-768.

Kierzek et al., (2001) Biophys Chem 91:1-20.

Ducruix et al., "Crystallization of Nucleic Acids and Proteins, A Practical Approach", Oxford University Press, New York 1999, p. 394.

Tang et al., Structural evidence for gene duplication in the evolution of the acid proteases: Feb. 1978, Nature, vol. 271, pp. 618-621.

Van Der Klei et al., <<Biosynthesis and assembly of alcohol oxidase, a peroxisomal matrix protein in methlotrophic yeasts: A review, Apr. 1991, Yeast, vol. 7, pp. 195-209.

Wang et al., "Crystallization of Glycosylated Human BACE Protease Domain Expressed in *Trichoplusia ni*", Biochimica et Biophysica Acta, (2004), vol. 1698, pp. 255-259.

Waugh, "Making the Most of Affinity Tags", Trends in Biotechnology, (2005), vol. 23, No. 6, pp. 316-320.

Witkowski, et al., "Conversion of a β-Ketoacyl Synthase to a Malonyl Decarboyylase by Replacement of the Active-Site Cysteine with Glutamine", Biochemistry, (1999), vol. 38, pp. 11643-11650.

Timasheff, "Crystallization", Encyclopedia of Molecular Biology, vol. 1, (1999), John Wiley-Interscience Publication, p. 586.

Branden et al., "Prediction, Engineering, and Design of Protein Structures," Introduction to Protein Structure, Garland Publishing, Inc., p. 247 (1991).

Wyckoff et al., "Diffraction Methods for Biological Marcomolecules," Methods in Enzymology, vol. 115, 4 pages (1985).

Budisa et al., "High-level biosynthetic substitution of methionine in proteins by its analogs 2-aminohexanoic acid, selenomethionine, telluromethionine and ethionine in *Escherichia coli*," Eur. J. Biochem FEBS, 230:788-796 (1995).

Wiencek, J.M., "New Strategies for Protein Crystal Growth," Annu. Rev. Biomed. Egn., 01:505-534 (1999).

Buts, Lieven et al., "Impact of natural variation in bacterial F17G adhesins on crystallization behaviour," Acta Cryst., D61, 1149-1159 (2005).

Skarzynski et al., "Industrial perspective on X-ray data collection and analysis," Acta Cryst., D62, 102-107 (2006).

Kundrot, C.E., "Which strategy for a protein crystallization project?", Cell. Mol. Life Sci., 61, 525-536 (2004).

Weber, Patricia C., "[2] Overview of Protein Crystallization Methods," Methods in Enzymology, 276:13-22 (1997).

Cudney, R., "Protein Crystallization and Dumb Luck," The Rigaku Journal, 16(1):1-7 (1999).

"Buffers," obtained at www.vanderbilt.edu/AnS/Chemistry/Rizzo/stuff/Buffers/buffers.html, last viewed on Mar. 12, 2008.

Benvenuti et al., "Crystallization of soluble proteins in vapor diffusion for x-ray crystallography," Nature Protocols, 2 (7):1633-1651 (2007).

Emmons et al., "Large-Scale Purification of Human BACE Expressed in Mammalian Cells and Removal of the Prosegment with HIV-1 Protease to Improve Crystal Diffraction," Protein and Peptide Letter, 15:119-130 (2008).

* cited by examiner

Fig. 6

SEQ ID NO: 1

```
BACE_ecoli_pQE70    -------MRGSFVEMVDNLRGKSGQGYYVEMTVGSPPQTLNILVDTGSSN
```
First residue visible (residue 61P) ⬈ ⬈ Residue 1

```
BACE_ecoli_pQE70    FAVGAAPHPFLHRYYQRQLSSTYRDLRKGVYVPYTQGKWEGELGTDLVSI

BACE_ecoli_pQE70    PHGPNVTVRANIAAITESDKFFINGSNWEGILGLAYAEIARPDDSLEPFF

BACE_ecoli_pQE70    DSLVKQTHVPNLFSLQLCGAGFPLNQSEVLASVGGSMIIGGIDHSLYTGS

BACE_ecoli_pQE70    LWYTPIRREWYYEVIIVRVEINGQDLKMDCKEYNYDKSIVDSGTTNLRLP

BACE_ecoli_pQE70    KKVFEAAVKSIKAASSTEKFPDGFWLGEQLVCWQAGTTPWNIFPVISLYL

BACE_ecoli_pQE70    MGEVTNQSFRITILPQQYLRPVEDVATSQDDCYKFAISQSSTGTVMGAVI

BACE_ecoli_pQE70    MEGFYVVFDRARKRIGFAVSACHVHDEFRTAAVEGPFVTLDMEDCGYNIP

BACE_ecoli_pQE70    QTDESRSHHHHHH
```

LIGAND SCREENING METHOD USING A CRYSTAL OF BETA SECRETASE

This application claims the benefit of U.S. Provisional Application No. 60/379,690, filed May 10, 2002, which is incorporated herein by reference in its entirety.

This application incorporates by reference the material contained on the duplicate (2) compact discs submitted herewith. Each disc contains the following file:

| Name | Size | Contents | Date of File Creation |
| --- | --- | --- | --- |
| table_1.txt | 268 kbytes | Table 1 | May 7, 2002 |
| table_2.txt | 273 kbytes | Table 2 | Nov. 15, 2001 |

FIELD OF THE INVENTION

This invention relates to the crystallization and structure determination of beta secretase, also known as BACE OR Asp2.

BACKGROUND

Alzheimer's disease (AD) causes progressive dementia with consequent formation of amyloid plaques, neurofibrillary tangles, gliosis and neuronal loss. The disease occurs in both genetic and sporadic forms whose clinical course and pathological features are quite similar. Three genes have been discovered to date which, when mutated, cause an autosomal dominant form of Alzheimer's disease. These encode the amyloid protein precursor (APP) and two related proteins, presenilin-1 (PS1) and presenilin-2 (PS2), which, as their names suggest, are structurally and functionally related. Mutations in any of the three proteins have been observed to enhance proteolytic processing of APP via an intracellular pathway that produces amyloid beta peptide (Aβ peptide, or sometimes here as Abeta), a 40-42 amino acid long peptide that is the primary component of amyloid plaque in AD.

Dysregulation of intracellular pathways for proteolytic processing may be central to the pathophysiology of AD. In the case of plaque formation, mutations in APP, PS1 or PS2 consistently alter the proteolytic processing of APP so as to enhance formation of Aβ 1-42, a form of the Aβ peptide which seems to be particularly amyloidogenic, and thus very important in AD. Different forms of APP range in size from 695-770 amino acids, localize to the cell surface, and have a single C-terminal transmembrane domain. The Abeta peptide is derived from a region of APP adjacent to and containing a portion of the transmembrane domain. Normally, processing of APP at the α-secretase site cleaves the midregion of the Aβ sequence adjacent to the membrane and releases the soluble, extracellular domain of APP from the cell surface. This α-secretase APP processing creates soluble APP-α, which is normal and not thought to contribute to AD. Pathological processing of APP at the β- and γ-secretase sites, which are located N-terminal and C-terminal to the α-secretase site, respectively, produces a very different result than processing at the α site. Sequential processing at the β- and γ-secretase sites releases the Aβ peptide, a peptide possibly very important in AD pathogenesis. Processing at the β- and γ-secretase sites can occur in both the endoplasmic reticulum (in neurons) and in the endosomal/lysosomal pathway after reinternalization of cell surface APP (in all cells). Despite intense efforts, for 10 years or more, to identify the enzymes responsible for processing APP at the β and γ sites, to produce the Aβ peptide, those proteases remained unknown until recently. The identification and characterization of the β secretase enzyme, termed Aspartyl Protease 2 (Asp2) has been established. Since the β-secretase catalyzes the committed step in formation of the Aβ peptide, it has become a key target in the search for therapeutic agents to combat Alzheimer's disease. It is believed that inhibition of BACE should slow or stop the onset of amyloid plaque formation and the associated symptoms of Alzheimer's disease.

In addition, the X-ray crystal structure of human BACE in complex with a peptide inhibitor was solved and published (Hong et al., *Science* 290:150-53 (2000)) from protein expressed in *E. coli* that contained no covalent sugar (glycosylation) at any of the four putative glycosylation sites within the enzyme.

SUMMARY OF THE INVENTION

In one aspect, the present invention provides a crystal of beta secretase. In one embodiment the crystal includes unliganded beta secretase. In another embodiment, the crystal has monoclinic space group symmetry $C222_1$. In another embodiment, the crystal includes a unit cell defined by the dimensions a, b, c, α, β, and γ, wherein a is about 55 Å to about 95 Å, b is about 84 Å to about 124 Å, c is about 80 Å to about 120 Å, and α=β=γ=90°. Methods of using the crystal in a drug screening assay are also provided.

In another embodiment, the present invention provides a method for crystallizing a human beta secretase molecule. In one embodiment, the method includes preparing purified human beta secretase in the substantial absence of a potential modifier, and crystallizing the human beta secretase from a solution having a pH of about 5.0 to about 5.6.

In another aspect, the present invention provides a method of preparing a crystal of liganded human beta secretase. In one embodiment, the method includes exposing a crystal of unliganded human beta secretase to a fluid including a ligand. Preferably, the exposing includes soaking.

In another aspect, the present invention provides a method of identifying the ability for a potential ligand to bind to BACE. In one embodiment, the method includes exposing a crystal of unliganded BACE to one or more samples including a potential ligand of BACE, and determining whether a ligand-BACE molecular complex is formed. Preferably the exposing includes soaking. Preferably, the one or more samples include a plurality of potential ligands.

In another aspect, the present invention provides a method of acquiring structural information for designing potential ligands for forming molecular complexes with BACE. In one embodiment, the method includes exposing a crystal of unliganded BACE to a library of potential ligands having diverse shapes, and determining whether a ligand-BACE molecular complex is formed.

In another aspect, the present invention provides an unliganded molecule including at least a portion of a human beta secretase or beta secretase-like binding pocket, wherein the binding pocket includes the amino acids listed in Table 3 and the binding pocket is defined by a set of points having a root mean square deviation of less than about 0.65 Å from points representing the backbone atoms of said amino acids as represented by the structure coordinates listed in Table 1.

In another aspect, the present invention provides a scalable three-dimensional configuration of points, at least a portion of said points derived from structure coordinates as listed in Table 1 of at least a portion of an unliganded human beta secretase molecule that includes a human beta secretase or beta secretase-like binding pocket. Preferably, the scalable three-dimensional configuration of points are displayed as a holographic image, a stereodiagram, a model, or a computer-displayed image.

In another aspect, the present invention provides a machine-readable data storage medium including a data storage material encoded with machine readable data which, when using a machine programmed with instructions for using said data, displays a graphical three-dimensional representation of a molecule. Preferably the molecule is an unliganded molecule including at least a portion of a human beta secretase or beta secretase-like binding pocket including the amino acids listed in Table 3, the binding pocket defined by a set of points having a root mean square deviation of less than about 0.65 Å from points representing the backbone atoms of said amino acids as represented by structure coordinates listed in Table 1 for a beta secretase or beta secretase-like molecule.

In another aspect, the present invention provides a method for obtaining structural information about a molecule or a molecular complex of unknown structure. In one embodiment, the method includes crystallizing the molecule or molecular complex; generating an x-ray diffraction pattern from the crystallized molecule or molecular complex; and applying to the x-ray diffraction pattern at least a portion of the structure coordinates as set forth in Table 1 for human beta secretase to generate a three-dimensional electron density map of at least a portion of the molecule or molecular complex whose structure is unknown.

In another aspect, the present invention provides a method for homology modeling a human beta secretase homolog. In one embodiment, the method includes aligning the amino acid sequence of a human beta secretase homolog with an amino acid sequence of human beta secretase and incorporating the sequence of the human beta secretase homolog into a model of human beta secretase formed from structure coordinates as set forth in Table 1 for human beta secretase to yield a preliminary model of the human beta secretase homolog; subjecting the preliminary model to energy minimization to yield an energy minimized model; and remodeling regions of the energy minimized model where stereochemistry restraints are violated to yield a final model of the human beta secretase homolog.

In another aspect, the present invention provides computer-assisted methods for identifying, designing, or making a potential modifier of human beta secretase activity. Preferably the methods include screening a library of chemical entities.

Abbreviations

The following abbreviations may be used throughout this disclosure:

Alzheimer's disease (AD)
3-[(1,1-Dimethylhydroxyethyl)amino]-2-hydroxy-1-propanesulfonic acid (AMPSO)
Amyloid beta peptide (Aβ peptide or Abeta)
Amyloid protein precursor (APP)
Aspartyl protease 2 (Asp2)
Beta amyloid cleaving enzyme (BACE, memapsin 2, beta secretase)
β-Mercaptoethanol (BME)
3-Cyclohexylamino-1-propanesulfonic acid (CAPS)
Dimethyl sulfoxide (DMSO)
Ethylenediaminetetraacetic acid (EDTA)
4-(2-Hydroxyethyl)-1-piperazineethanesulfonic acid (HEPES)
2-Methyl-2,4-pentanediol (MPD)
4-Morpholineethanesulfonic acid (MES)
Multiple anomalous dispersion (MAD)
Presenilin-1 (PS1)
Presenilin-2 (PS2)
Poly(ethylene glycol) (PEG)
2-Amino-2-hydroxymethyl-1,3-propanediol (TRIS)
TE-TRIS-EDTA The following amino acid abbreviations are used throughout this disclosure:

| A = Ala = Alanine | T = Thr = Threonine |
|---|---|
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

BRIEF DESCRIPTION OF THE FIGURES

FIG. 6 depicts the sequences of the *E. coli* construct for recombinant human BACE (SEQ ID NO:1) used to obtain the crystals described. The first visible residue in the crystal structures is indicated.

DETAILED DESCRIPTION OF THE PREFERRED EMBODIMENTS

Figure 1:
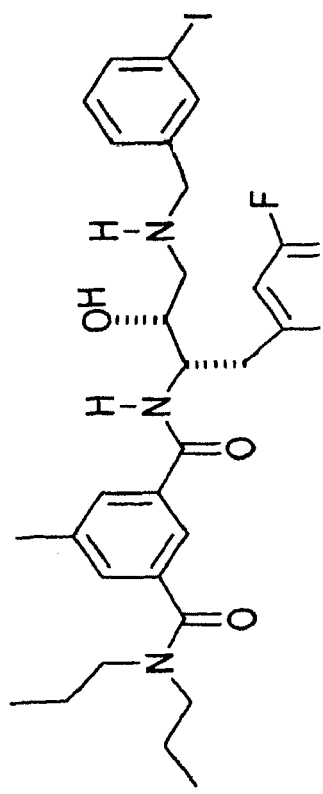
FIG. 1 is an illustration of the chemical structure of an inhibitor used in co-crystallization experiments.

Tables 1 and 2 list atomic structure coordinates derived by x-ray diffraction of crystals having space groups C222$_1$ and C2, respectively, of human BACE expressed in *E. coli*. Column 2 lists a number for the atom in the structure. Column 3 lists the element whose coordinates are measured. The first letter in the column defines the element. Column 4 lists the type of amino acid. Column 5 lists a number for the amino acid in the structure. Columns 6-8 list the crystallographic coordinates X, Y, and Z respectively. The crystallographic coordinates define the atomic position of the element measured. Column 9 lists an occupancy factor that refers to the fraction of the molecules in which each atom occupies the position specified by the coordinates. A value of "1" indicates that each atom has the same conformation, i.e., the same position, in all molecules of the crystal. Column 10 lists a thermal factor "B" that measures movement of the atom around its atomic center. Column 11 lists the chain id (AA for molecule A in the asymmetric unit, BB for molecule B in the asymmetric unit, CC for molecule C in the asymmetric unit, WW for water molecules, and LL for inhibitor molecules). Column 12 lists the element whose coordinates are measured.

Crystalline Form(s) and Method of Making

The three-dimensional structure of human beta secretase was solved using x-ray crystallography to 1.7 Å resolution for an unliganded beta secretase crystal. Preferably the beta secretase is isolated from *E. coli*. As used herein, "unliganded" means that the molecule does not include substantial amounts of active sites having a ligand complexed thereto. As used herein, "ligand" refers to a chemical entity that can form a reversible complex with the protein and that could function as a drug candidate (e.g., modifiers and inhibitors). Thus, the term "ligand" as used herein does not include chemical entities that could not function as a drug candidate (e.g., water, metal ions, and solvents). Preferably, an unliganded crystal includes at least about 70% unliganded active sites, more preferably at least about 90% unliganded active sites, even more preferably at least about 95% unliganded active sites, and most preferably about 100% unliganded active sites.

Inspection of the active site revealed an absence of inhibitor in the electron density map and a movement of the active site flap away from the rest of the protein molecule. This discovery led to the first unliganded structure of BACE which was refined to an R-factor of 23.3% and a Free R-factor of 26.8% (Table 10). Details of this structure are described herein.

Preferably, the crystal has monoclinic space group symmetry $C222_1$. Preferably, the crystal includes monoclinic shaped unit cells, each unit cell having dimensions a=75±20 Å, b=104±20 Å, c=100±20 Å, and $\alpha=\beta=\gamma 90°$. More preferably, the crystal includes monoclinic shaped unit cells, each unit cell having dimensions a=75±5 Å, b=104±5 Å, c=100±5 Å, and $\alpha=\beta=\gamma=90°$. Most preferably, the crystal includes tetragonal shaped unit cells, each unit cell having dimensions a=75 Å, b=104 Å, c=100 Å, and $\alpha=\beta=\gamma=90°$. Preferably, the crystallized enzyme is a monomer with one monomer in the asymmetric unit. Preferably, human beta secretase is isolated from an *E. coli* strain, for example, from expression construct pQE70 with the propeptide removed and possessing a C-terminal His-6 tag.

In a preferred embodiment, protein is prepared either by first concentrating the protein in the presence of about a 2.4 molar excess of about 100% DMSO, or by the addition of about 1 mM to about 2 mM DMSO to the concentrated protein sample (preferably about 6 mg/ml to about 8 mg/ml).

Unliganded crystals are preferably grown in the substantial absence of potential modifiers (e.g., inhibitors), preferably using a PEG as a precipitant. Preferably, the PEG has a number average molecular weight of at most about 10,000 Daltons, more preferably at most about 1,000 Daltons, and most preferably at most about 500 Daltons. Preferably, the PEG has a number average molecular weight of at least about 100 Daltons, more preferably at least about 150 Daltons, and most preferably at least about 175 Daltons. A preferred PEG includes PEG 200. Preferably, at least about 10% (w/v), and more preferably at least about 24% (w/v) PEG 200 is used as precipitant, based on the total volume of solution. Preferably, at most about 50% (w/v), and more preferably at most about 39% (w/v) PEG 200 is used as precipitant, based on the total volume of solution.

Preferably, the crystallization solution is buffered to about pH 5.0 to about pH 5.6 using a buffer. Preferably, the buffer has a $pK_a$ of about 3 to about 6. Preferred buffers include, for example, sodium acetate. When sodium acetate is used as a buffer, it is preferably used at a concentration of about 1 mM to about 200 mM. Typically, no additional salt is present during crystallization. However, the solution may optionally include an additional salt, such as, for example, sodium chloride, ammonium sulfate, magnesium sulfate, lithium sulfate, sodium acetate, and combinations thereof. If the optional salt is present, the solution preferably includes about 0.001 M to about 0.5 M of the salt. Optionally, the solution may include an organic solvent, preferably at most about 40% by weight organic solvent. Preferred solvents include, for example, dimethylsulfoxide or 2-methyl-2,4-pentanediol.

Streak seeding at setup is preferred for optimal crystal growth. A cat whisker may be used to seed at setup with a thousand fold dilution of seed stock. Crystals may be slowly grown over a number of days, for example, 14 days. The crystal morphology preferably includes single rods with an approximate size of 0.25×0.15×0.15 mm.

Variation in buffer and buffer pH as well as other additives such as PEG, PEG-MME, PEG-DME, or polyoxyalkylenepolyamines is apparent to those skilled in the art and may result in similar crystals.

The invention further includes a human beta secretase crystal that is isomorphous with a human beta secretase crystal having a unit cell defined by the dimensions of a, b, c, $\alpha$, $\beta$, and $\gamma$, wherein a is about 55 Å to about 95 Å, b is about 84 Å to about 124 Å, c is about 80 Å to about 120 Å; and $\alpha=\beta=\gamma=90°$.

Soaking Protocol to Incorporate Ligands

The $C222_1$ unliganded crystal form led to several experiments to test its utility in BACE-ligand molecular complex formation. As used herein, a "molecular complex" means a protein in covalent or non-covalent association with a chemical entity (e.g., a ligand). Crystal forms that possess large enough solvent channels can be used to form complexes by soaking ligands into the crystal. Experiments with the inhibitor shown in FIG. 1 revealed that this ligand (e.g., an inhibitor) could be successfully added to the crystallization drop (after formation of the unliganded crystals) in order to form a complex with BACE. Various other inhibitors of different levels of potency were tested in order to define the parameters for soaking compounds into these unliganded crystals.

Addition of a stabilization solution containing about 1 mM to about 10 mM of a BACE inhibitor ($IC_{50} \leq 10$ μM) to the crystallization drop provided conditions for formation of a BACE-inhibitor complex. No additional cryoprotectant was needed as the crystallization conditions were cryogenic. The inhibitor shown in FIG. 1 was successfully soaked into these unliganded crystals to form a complex consistent with earlier X-ray structures prepared by co-crystallization.

Routine use of the $C222_1$ crystal form for the preparation of BACE-ligand complexes significantly reduces the time between receipt of a compound for testing and generation of a complex. Because separate co-crystallization experiments are not required for each compound, complexes can be generated within a few days and subsequently data can be collected. The higher symmetry of the $C222_1$ crystal form provides an added advantage over the C2 crystal form in that 50% less data is required for a complete dataset reducing the time required for data collection. There are occasions when soaking an inhibitor into the $C222_1$ crystal form did not result in a BACE-inhibitor complex as expected due to low solubility of the compound in the soaking conditions or other unexplained factors. In these cases, the C2 crystal form provided an alternative for complex preparation.

Crystallography may preferably be used to screen and identify chemical entities that are not known ligands of target biomolecules as disclosed, for example, in U.S. Pat. No. 6,297,021 (Nienaber et al.). For example, crystallography may preferably be used to screen and identify chemical entities that are not known ligands of BACE for their ability to bind to BACE. A preferred method includes obtaining a crystal of unliganded BACE; exposing the unliganded BACE to one or more test samples that include a potential ligand of the BACE; and determining whether a ligand-BACE molecular complex is formed. The BACE may be exposed to potential ligands by various methods including, for example, soaking a BACE crystal in a solution of one or more potential ligands, or co-crystallizing BACE in the presence of one or more potential ligands.

Structural information from the ligand-BACE complexes found may preferably be used to design new ligands that bind tighter, bind more specifically, have desired biological activity properties, have better safety profiles than known ligands, and combinations thereof. For example, libraries of "shape-diverse" chemical entities may preferably be used to allow direct identification of the ligand-BACE complex even when the ligand is exposed as part of a mixture. As used herein, "shape diverse" refers to ligands having substantial differences in three-dimensional shapes that can be recognized, for example, by visual inspection of the two dimensional chemical structures, or by calculation and comparison of relevant parameters by a computational program. Shape diversity of the mixture permits a bound ligand to be identified directly from the resultant electron density map. This preferably avoids the need for time-consuming deconvolution of a hit from the mixture. Here, three important steps are preferably achieved simultaneously. Preferably, the calculated electron density function directly reveals the binding event, identifies the bound chemical entity, and provides a detailed 3-D structure of the ligand-BACE complex. Once a hit is found, preferably a number of analogs or derivatives of the hit may be screened for tighter binding or desired biological activity by traditional screening methods. Moreover, the identity of the hit and information about structure of the target may preferably be used to develop analogs or derivatives with tighter binding or desired biological activity properties. Optionally, the ligand-BACE complex may be exposed to additional iterations of potential ligands so that two or more hits may preferably be linked together to identify or design a more potent ligand.

X-Ray Crystallographic Analysis

Each of the constituent amino acids of human beta secretase is defined by a set of structure coordinates as set forth in Table 1. The term "structure coordinates" refers to Cartesian coordinates derived from mathematical equations related to the patterns obtained on diffraction of a monochromatic beam of x-rays by the atoms (scattering centers) of a human beta secretase complex in crystal form. The diffraction data are used to calculate an electron density map of the repeating unit of the crystal. The electron density maps are then used to establish the positions of the individual atoms of the human beta secretase protein or protein/ligand complex.

Slight variations in structure coordinates can be generated by mathematically manipulating the human beta secretase or human beta secretase/ligand structure coordinates. For example, the structure coordinates set forth in Table 1 could be manipulated by crystallographic permutations of the structure coordinates, fractionalization of the structure coordinates, integer additions or subtractions to sets of the structure coordinates, inversion of the structure coordinates or any combination of the above. Alternatively, modifications in the crystal structure due to mutations, additions, substitutions, and/or deletions of amino acids, or other changes in any of the components that make up the crystal, could also yield variations in structure coordinates. Such slight variations in the individual coordinates will have little effect on overall shape. If such variations are within an acceptable standard error as compared to the original coordinates, the resulting three-dimensional shape is considered to be structurally equivalent. Structural equivalence is described in more detail below.

It should be noted that slight variations in individual structure coordinates of the human beta secretase would not be expected to significantly alter the nature of chemical entities such as ligands that could associate with the binding pockets. In this context, the phrase "associating with" refers to a condition of proximity between a chemical entity, or portions thereof, and a human beta secretase molecule or portions thereof. The association may be non-covalent, wherein the juxtaposition is energetically favored by hydrogen bonding, van der Waals forces, or electrostatic interactions, or it may be covalent. Thus, for example, a ligand that bound to a binding pocket of human beta secretase would also be expected to bind to or interfere with a structurally equivalent binding pocket.

For the purpose of this invention, any molecule or molecular complex or binding pocket thereof, or any portion thereof, that has a root mean square deviation of conserved residue backbone atoms (N, Cα, C, O) of less than about 0.65 Å, when superimposed on the relevant backbone atoms described by the reference structure coordinates listed in Table 1, is considered "structurally equivalent" to the reference molecule. That is to say, the crystal structures of those portions of the two molecules are substantially identical, within acceptable error. As used herein, "residue" refers to one or more atoms. Particularly preferred structurally equivalent molecules or molecular complexes are those that are defined by the entire set of structure coordinates listed in Table 1± a root mean square deviation from the conserved backbone atoms of those amino acids of less than about 0.65 Å. More preferably, the root mean square deviation is at most about 0.5 Å, and even more preferably, at most about 0.35 Å. Other embodiments of this invention include a molecular complex defined by the structure coordinates listed in Table 1 for those amino acids listed in Table 3, Table 4, or Table 5, ± a root mean square deviation from the conserved backbone atoms of those amino acids of less than about 0.65 Å, preferably at most about 0.5 Å, and more preferably at most about 0.35 Å.

The term "root mean square deviation" means the square root of the arithmetic mean of the squares of the deviations. It is a way to express the deviation or variation from a trend or object. For purposes of this invention, the "root mean square deviation" defines the variation in the backbone of a protein from the backbone of human beta secretase or a binding pocket portion thereof, as defined by the structure coordinates of human beta secretase described herein.

It will be readily apparent to those of skill in the art that the numbering of amino acids in other isoforms of human beta secretase may be different than that of human beta secretase expressed in *E. coli*.

Active Site and Other Structural Features

Applicants' invention provides information about the shape and structure of the binding pocket of human beta secretase in the presence of a potential modifier. The secondary structure of the human beta secretase monomer includes two domains consistent with a typical aspartic protease fold.

Binding pockets are of significant utility in fields such as drug discovery. The association of natural ligands or substrates with the binding pockets of their corresponding receptors or enzymes is the basis of many biological mechanisms of action. Similarly, many drugs exert their biological effects through association with the binding pockets of receptors and enzymes. Such associations may occur with all or any parts of the binding pocket. An understanding of such associations helps lead to the design of drugs having more favorable associations with their target, and thus improved biological effects. Therefore, this information is valuable in designing potential modifiers of beta secretase-like binding pockets, as discussed in more detail below.

The term "binding pocket," as used herein, refers to a region of a molecule or molecular complex, that, as a result of its shape, favorably associates with another chemical entity. Thus, a binding pocket may include or consist of features such as cavities, surfaces, or interfaces between domains. Chemical entities that may associate with a binding pocket include, but are not limited to, cofactors, substrates, modifiers, agonists, and antagonists.

The amino acid constituents of a human beta secretase binding pocket as defined herein are positioned in three dimensions in accordance with the structure coordinates listed in Table 1 and/or Table 2. In one aspect, the structure coordinates defining a binding pocket of human beta secretase include structure coordinates of all atoms in the constituent amino acids; in another aspect, the structure coordinates of a binding pocket include structure coordinates of just the backbone atoms of the constituent amino acids.

The binding pocket of human beta secretase preferably includes the amino acids listed in Table 3, more preferably the amino acids listed in Table 4, and most preferably the amino acids listed in Table 5, as represented by the structure coordinates listed in Table 1 and/or Table 2. Alternatively, the binding pocket of human beta secretase may be defined by those amino acids whose backbone atoms are situated within about 4 Å, more preferably within about 7 Å, most preferably within about 10 Å, of one or more constituent atoms of a bound substrate or modifier. In yet another alternative, the binding pocket may be defined by those amino acids whose backbone atoms are situated within a sphere centered on the coordinates representing the alpha carbon atom of residue Thr 231, the sphere having a radius of about 15 Å, preferably about 20 Å, and more preferably about 25 Å.

The term "beta secretase-like binding pocket" refers to a portion of a molecule or molecular complex whose shape is sufficiently similar to at least a portion of a binding pocket of human beta secretase as to be expected to bind related structural analogues. As used herein, "at least a portion" means that at least about 50% of the amino acids are included, preferably at least about 70% of the amino acids are included, more preferably at least about 90% of the amino acids are included, and most preferably all the amino acids are included. A structurally equivalent binding pocket is defined by a root mean square deviation from the structure coordinates of the backbone atoms of the amino acids that make up binding pockets in human beta secretase (as set forth in Table 1) of at most about 0.35 Å. How this calculation is obtained is described below.

Accordingly, the invention provides molecules or molecular complexes including a human beta secretase binding pocket or beta secretase-like binding pocket, as defined by the sets of structure coordinates described above.

TABLE 3

Residues with 4 Å of a binding site.

| GLY | 11 | GLY | 12 | GLY | 13 | LEU | 30 |
|---|---|---|---|---|---|---|---|
| ASP | 32 | GLY | 34 | SER | 35 | PRO | 70 |
| TYR | 71 | THR | 72 | GLN | 73 | GLY | 74 |
| PHE | 108 | ILE | 110 | TRP | 115 | TYR | 198 |
| ASP | 228 | GLY | 230 | THR | 231 | THR | 232 |
| ARG | 235 | | | | | | |

TABLE 4

Residues with 7 Å of a binding site.

| LYS | 9 | GLY | 11 | GLN | 12 | GLY | 13 |
|---|---|---|---|---|---|---|---|
| TYR | 14 | LEU | 30 | ASP | 32 | THR | 33 |
| GLY | 34 | SER | 35 | SER | 36 | ASN | 37 |
| VAL | 69 | PRO | 70 | TYR | 71 | THR | 72 |
| GLN | 73 | GLY | 74 | LYS | 75 | TRP | 76 |
| ASP | 106 | LYS | 107 | PHE | 108 | PHE | 109 |
| ILE | 110 | TRP | 115 | ILE | 118 | ILE | 126 |
| ALA | 127 | ARG | 128 | TYR | 198 | LYS | 224 |
| ILE | 226 | ASP | 228 | SER | 229 | GLY | 230 |
| THR | 231 | THR | 232 | ASN | 233 | ARG | 235 |
| SER | 325 | GLN | 326 | THR | 329 | VAL | 332 |
| ALA | 335 | | | | | | |

TABLE 5

Residues with 10 Å of a binding site.

| ARG | 7 | GLY | 8 | LYS | 9 | SER | 10 |
|---|---|---|---|---|---|---|---|
| GLY | 11 | GLN | 12 | GLY | 13 | TYR | 14 |
| TYR | 15 | ILE | 29 | LEU | 30 | VAL | 31 |
| ASP | 32 | THR | 33 | GLY | 34 | SER | 35 |
| SER | 36 | ASN | 37 | PHE | 38 | PHE | 47 |
| TYR | 68 | VAL | 69 | PRO | 70 | TYR | 71 |
| THR | 72 | GLN | 73 | GLY | 74 | LYS | 75 |
| TRP | 76 | ILE | 102 | SER | 105 | ASP | 106 |
| LYS | 107 | PHE | 108 | PHE | 109 | ILE | 110 |
| ASN | 111 | SER | 113 | ASN | 114 | TRP | 115 |
| GLU | 116 | GLY | 117 | ILE | 118 | LEU | 119 |
| GLY | 120 | LEU | 121 | ALA | 122 | TYR | 123 |
| ALA | 124 | GLU | 125 | ILE | 126 | ALA | 127 |
| ARG | 128 | PRO | 129 | LEU | 154 | LEU | 167 |
| VAL | 170 | TRP | 197 | TYR | 198 | TYR | 199 |
| ASP | 223 | LYS | 224 | SER | 225 | ILE | 226 |
| VAL | 227 | ASP | 228 | SER | 229 | GLY | 230 |
| THR | 231 | THR | 232 | ASN | 233 | LEU | 234 |
| ARG | 235 | LEU | 236 | GLY | 264 | ARG | 307 |
| LYS | 321 | ALA | 323 | ILE | 324 | SER | 325 |
| GLN | 326 | SER | 327 | SER | 328 | THR | 329 |
| GLY | 330 | THR | 331 | VAL | 332 | MET | 333 |
| GLY | 334 | ALA | 335 | VAL | 336 | GLU | 339 |

Overview of Liganded and Unliganded Structures.

The structure of BACE was reported in the literature in October 2000 (Hong et al., *Science* 290:150-53 (2000)) and made available through the Protein Data Bank (id code: 1FKN). BACE is comprised of two domains that correspond to the N- and C-terminal portions of the protein. The protein fold is similar to the structures of other aspartic proteases solved by X-ray crystallography. The secondary structure of the protein core is primarily beta sheet with several alpha helices on the surface of the protein. The 1 FKN structure and the structure solved herein do not contain the transmembrane domain found in the wildtype protein. This domain has been removed for ease of protein expression, purification, and crystallization.

Figure 3:
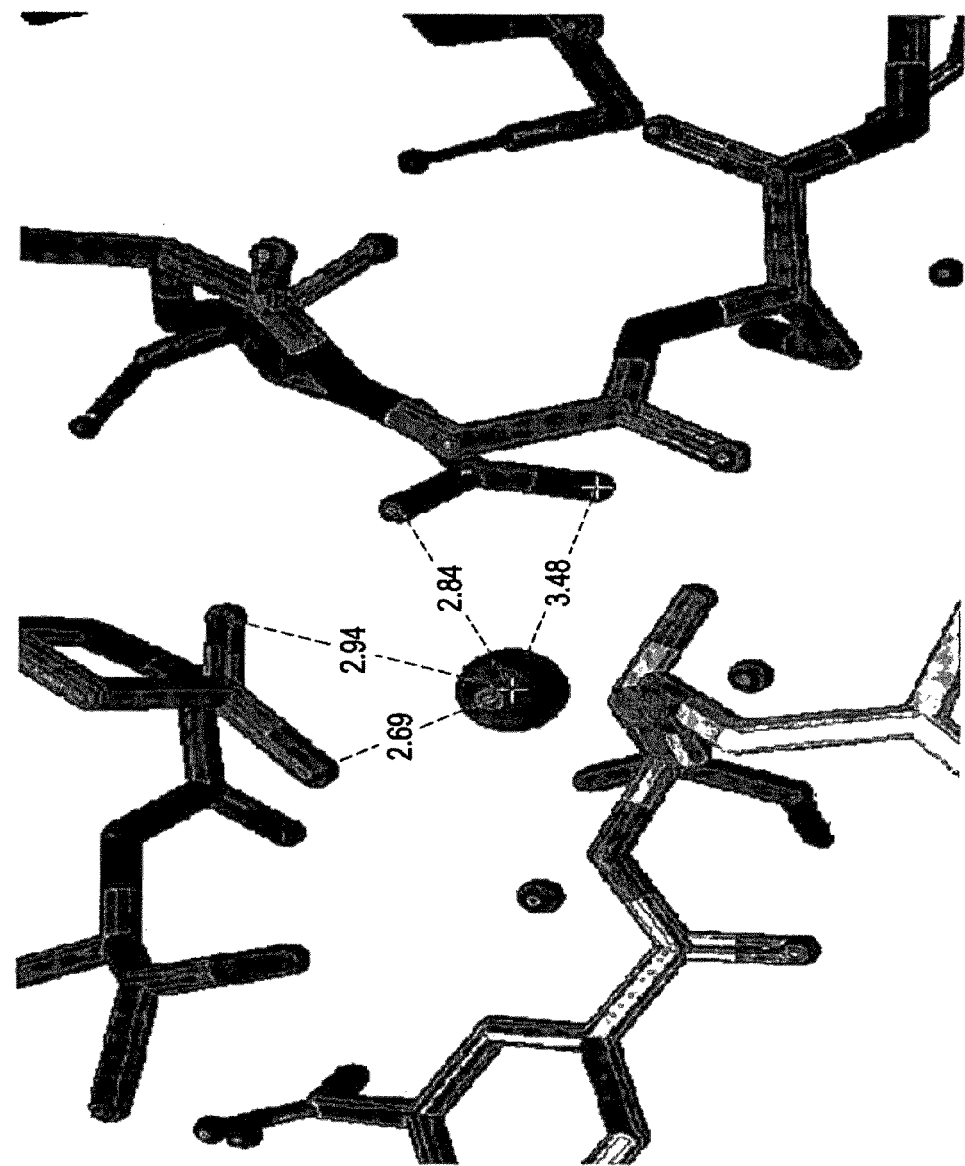
FIG. 3 illustrates a close-up view of the water bound to the catalytic aspartates (Asp 32 and 228) in the unliganded structure. This water is displaced when the inhibitor shown in FIG. 1 binds to the enzyme shown in the lower left.
Figure 4A:
FIG. 4 depicts three stereoviews comparing the liganded and unliganded forms of BACE. a) Overview of the entire molecule showing differences localized to the flap and adjacent beta strands. b) A close-up view of the active site showing main chain backbone changes near the arrow. c) Similar view as (b) with the flap side chains visible near the arrow.
Figure 4B:
Figure 4C:
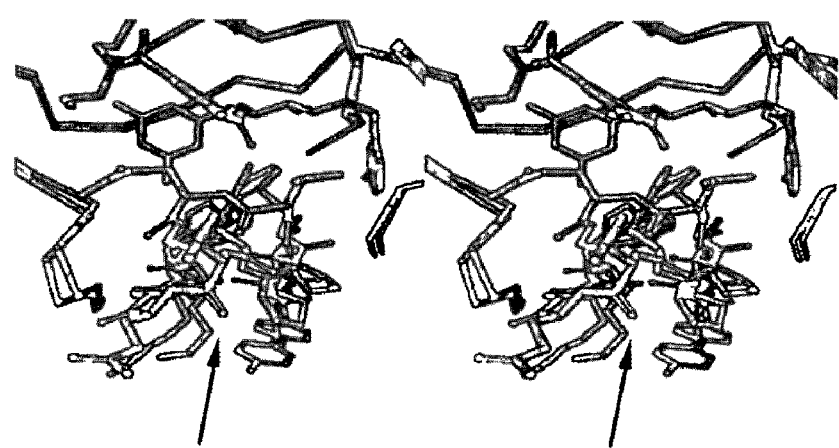
Figure 5B:
FIG. 5 depicts a comparison of active site surfaces in a) liganded and b) unliganded BACE. The ligand is the inhibitor shown in FIG. 1, and it is illustrated in b) for reference only.
Figure 5A:
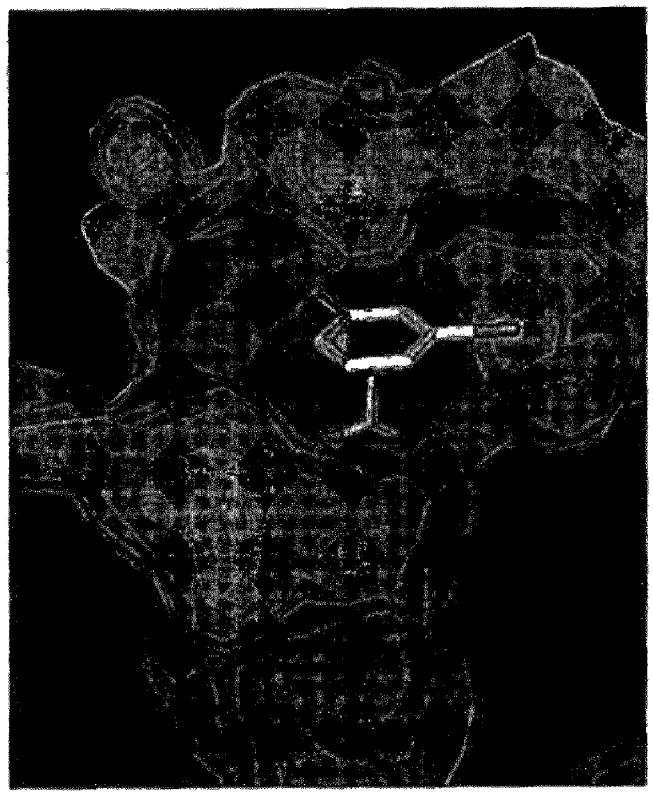

The inhibitor shown in FIG. 1 sits at the active site between the catalytic aspartates (residues 32 and 228) and the flap (residues 66-76). In the liganded structure the flap is closed down over the ligand making a single hydrogen bond and several van der Waals contacts. The presence of the ligand displaces a bound water molecule observed in the unliganded structure to interact directly with the catalytic aspartates (FIG. 3). In the unliganded structure, the flap (residues 66-76) and the adjacent beta strands (residues 101-107 and 42-47) move away from the core of the protein (FIG. 4). The Cα of Gln 73 moves 5.9 Å away from its position in the liganded structure, while the Cα of Thr72 moves 3.7 Å away from its position in the liganded structure. The flap undergoes not only movement away from the active site but also a twisting motion which moves the left hand portion of the flap further away from the active site. The result of this motion is a more open active site and a change in the topology of the P1 and P2' pockets.

Three-Dimensional Configurations

X-ray structure coordinates define a unique configuration of points in space. Those of skill in the art understand that a set of structure coordinates for protein or an protein/ligand complex, or a portion thereof, define a relative set of points that, in turn, define a configuration in three dimensions. A similar or identical configuration can be defined by an entirely different set of coordinates, provided the distances and angles between coordinates remain essentially the same. In addition, a scalable configuration of points can be defined by increasing or decreasing the distances between coordinates by a scalar factor while keeping the angles essentially the same.

The present invention thus includes the scalable three-dimensional configuration of points derived from the structure coordinates of at least a portion of a human beta secretase molecule or molecular complex, as listed in Table 1, as well as structurally equivalent configurations, as described below. Preferably, the scalable three-dimensional configuration includes points derived from structure coordinates representing the locations of a plurality of the amino acids defining a human beta secretase binding pocket.

In one embodiment, the scalable three-dimensional configuration includes points derived from structure coordinates representing the locations the backbone atoms of a plurality of amino acids defining the human beta secretase binding pocket, preferably the amino acids listed in Table 3, more preferably the amino acids listed in Table 4, and most preferably the amino acids listed in Table 5. Alternatively, the scalable three-dimensional configuration includes points derived from structure coordinates representing the locations of the side chain and the backbone atoms (other than hydrogens) of a plurality of the amino acids defining the human beta secretase binding pocket, preferably the amino acids listed in Table 3, more preferably the amino acids listed in Table 4, and most preferably the amino acids listed in Table 5.

Likewise, the invention also includes the scalable three-dimensional configuration of points derived from structure coordinates of molecules or molecular complexes that are structurally homologous to beta secretase, as well as structurally equivalent configurations. Structurally homologous molecules or molecular complexes are defined below. Advantageously, structurally homologous molecules can be identified using the structure coordinates of human beta secretase according to a method of the invention.

The configurations of points in space derived from structure coordinates according to the invention can be visualized as, for example, a holographic image, a stereodiagram, a model, or a computer-displayed image, and the invention thus includes such images, diagrams or models.

Structurally Equivalent Crystal Structures

Various computational analyses can be used to determine whether a molecule or a binding pocket portion thereof is "structurally equivalent," defined in terms of its three-dimensional structure, to all or part of human beta secretase or its binding pockets. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. The procedure used in Molecular Similarity to compare structures is divided into four steps: (1) load the structures to be compared; (2) define the atom equivalences in these structures; (3) perform a fitting operation; and (4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention equivalent atoms are defined as protein backbone atoms (N, Cα, C, and O) for all conserved residues between the two structures being compared. A conserved residue is defined as a residue which is structurally or functionally equivalent. Only rigid fitting operations are considered.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

Machine Readable Storage Media

Transformation of the structure coordinates for all or a portion of human beta secretase or the human beta secretase/ligand complex or one of its binding pockets, for structurally homologous molecules as defined below, or for the structural equivalents of any of these molecules or molecular complexes as defined above, into three-dimensional graphical representations of the molecule or complex can be conveniently achieved through the use of commercially-available software.

The invention thus further provides a machine-readable storage medium including a data storage material encoded with machine readable data which, when using a machine programmed with instructions for using said data, displays a graphical three-dimensional representation of any of the molecule or molecular complexes of this invention that have been described above. In a preferred embodiment, the machine-readable data storage medium includes a data storage material encoded with machine readable data which, when using a machine programmed with instructions for using said data, displays a graphical three-dimensional representation of a molecule or molecular complex including all or any parts of a human beta secretase binding pocket or an beta secretase-like binding pocket, as defined above. In another preferred embodiment, the machine-readable data storage medium includes a data storage material encoded with machine readable data which, when using a machine programmed with instructions for using said data, displays a graphical three-dimensional representation of a molecule or molecular complex defined by the structure coordinates of all of the amino acids listed in Table 1, ± a root mean square deviation from the backbone atoms of said amino acids of less than about 0.65 Å, more preferably at most about 0.5 Å, and even more preferably, at most about 0.35 Å.

In an alternative embodiment, the machine-readable data storage medium includes a data storage material encoded with a first set of machine readable data which includes the Fourier transform of the structure coordinates set forth in Table 1, and which, when using a machine programmed with instructions for using said data, can be combined with a second set of machine readable data including the x-ray diffraction pattern of a molecule or molecular complex to determine at least a portion of the structure coordinates corresponding to the second set of machine readable data.

For example, a system for reading a data storage medium may include a computer including a central processing unit ("CPU"), a working memory which may be, e.g., RAM (random access memory) or "core" memory, mass storage memory (such as one or more disk drives or CD-ROM drives), one or more display devices (e.g., cathode-ray tube ("CRT") displays, light emitting diode ("LED") displays, liquid crystal displays ("LCDs"), electroluminescent displays, vacuum fluorescent displays, field emission displays ("FEDs"), plasma displays, projection panels, etc.), one or more user input devices (e.g., keyboards, microphones, mice, track balls, touch pads, etc.), one or more input lines, and one or more output lines, all of which are interconnected by a conventional bidirectional system bus. The system may be a stand-alone computer, or may be networked (e.g., through local area networks, wide area networks, intranets, extranets, or the internet) to other systems (e.g., computers, hosts, servers, etc.). The system may also include additional computer controlled devices such as consumer electronics and appliances.

Input hardware may be coupled to the computer by input lines and may be implemented in a variety of ways. Machine-readable data of this invention may be inputted via the use of a modem or modems connected by a telephone line or dedicated data line. Alternatively or additionally, the input hardware may include CD-ROM drives or disk drives. In conjunction with a display terminal, a keyboard may also be used as an input device.

Output hardware may be coupled to the computer by output lines and may similarly be implemented by conventional devices. By way of example, the output hardware may include a display device for displaying a graphical representation of a binding pocket of this invention using a program such as QUANTA as described herein. Output hardware might also include a printer, so that hard copy output may be produced, or a disk drive, to store system output for later use.

In operation, a CPU coordinates the use of the various input and output devices, coordinates data accesses from mass storage devices, accesses to and from working memory, and determines the sequence of data processing steps. A number of programs may be used to process the machine-readable data of this invention. Such programs are discussed in reference to the computational methods of drug discovery as described herein. References to components of the hardware system are included as appropriate throughout the following description of the data storage medium.

Machine-readable storage devices useful in the present invention include, but are not limited to, magnetic devices, electrical devices, optical devices, and combinations thereof. Examples of such data storage devices include, but are not limited to, hard disk devices, CD devices, digital video disk devices, floppy disk devices, removable hard disk devices, magneto-optic disk devices, magnetic tape devices, flash memory devices, bubble memory devices, holographic storage devices, and any other mass storage peripheral device. It should be understood that these storage devices include necessary hardware (e.g., drives, controllers, power supplies, etc.) as well as any necessary media (e.g., disks, flash cards, etc.) to enable the storage of data.

Structurally Homologous Molecules, Molecular Complexes, and Crystal Structures

The structure coordinates set forth in Table 1 can be used to aid in obtaining structural information about another crystallized molecule or molecular complex. The method of the invention allows determination of at least a portion of the three-dimensional structure of molecules or molecular complexes which contain one or more structural features that are similar to structural features of human beta secretase. These molecules are referred to herein as "structurally homologous" to human beta secretase. Similar structural features can include, for example, regions of amino acid identity, conserved active site or binding site motifs, and similarly arranged secondary structural elements (e.g., α helices and β sheets). Optionally, structural homology is determined by aligning the residues of the two amino acid sequences to optimize the number of identical amino acids along the lengths of their sequences; gaps in either or both sequences are permitted in making the alignment in order to optimize the number of identical amino acids, although the amino acids in each sequence must nonetheless remain in their proper order. Preferably, two amino acid sequences are compared using the Blastp program, version 2.0.9, of the BLAST 2 search algorithm, as described by Tatusova et al., *FEMS Microbiol Lett* 174, 247-50 (1999). Preferably, the default values for all BLAST 2 search parameters are used, including matrix=BLOSUM62; open gap penalty=11, extension gap penalty=1, gap x_dropoff=50, expect=10, wordsize=3, and filter on. In the comparison of two amino acid sequences using the BLAST search algorithm, structural similarity is referred to as "identity." Preferably, a structurally homologous molecule is a protein that has an amino acid sequence sharing at least 65% identity with a native or recombinant amino acid sequence of human beta secretase (for example, SEQ ID NO:1). More preferably, a protein that is structurally homologous to human beta secretase includes at least one contiguous stretch of at least 50 amino acids that shares at least 80% amino acid sequence identity with the analogous portion of the native or recombinant human beta secretase (for example, SEQ ID NO:1). Methods for generating structural information about the structurally homologous molecule or molecular complex are well-known and include, for example, molecular replacement techniques.

Therefore, in another embodiment this invention provides a method of utilizing molecular replacement to obtain structural information about a molecule or molecular complex whose structure is unknown including the steps of:

(a) crystallizing the molecule or molecular complex of unknown structure;

(b) generating an x-ray diffraction pattern from said crystallized molecule or molecular complex; and (c) applying at least a portion of the structure coordinates set forth in Table 1 to the x-ray diffraction pattern to generate a three-dimensional electron density map of the molecule or molecular complex whose structure is unknown.

By using molecular replacement, all or part of the structure coordinates of human beta secretase or the human beta secretase/ligand complex as provided by this invention can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that cannot be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a structurally homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of human beta secretase or the human beta secretase/modifier complex within the unit cell of the crystal of the unknown molecule or molecular complex so as best to account for the observed x-ray diffraction pattern of the crystal of the molecule or molecular complex whose structure is unknown. Phases can then be calculated from this model and combined with the observed x-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex (Lattman, *Meth. Enzymol.,* 115, 55-77 (1985); M. G. Rossman, ed., "The Molecular Replacement Method," *Int. Set. Rev. Ser.*, No. 13, Gordon & Breach, New York (1972)).

Structural information about a portion of any crystallized molecule or molecular complex that is sufficiently structurally homologous to a portion of human beta secretase can be resolved by this method. In addition to a molecule that shares one or more structural features with human beta secretase as described above, a molecule that has similar bioactivity, such as the same catalytic activity, substrate specificity or ligand binding activity as human beta secretase, may also be sufficiently structurally homologous to human beta secretase to permit use of the structure coordinates of human beta secretase to solve its crystal structure.

In a preferred embodiment, the method of molecular replacement is utilized to obtain structural information about a molecule or molecular complex, wherein the molecule or molecular complex includes a human beta secretase subunit or homolog. A "subunit" of human beta secretase is a human beta secretase molecule that has been truncated at the N-terminus or the C-terminus, or both. In the context of the present invention, a "homolog" of human beta secretase is a protein that contains one or more amino acid substitutions, deletions, additions, or rearrangements with respect to the amino acid sequence of human beta secretase (SEQ ID NO:1), but that, when folded into its native conformation, exhibits or is reasonably expected to exhibit at least a portion of the tertiary (three-dimensional) structure of human beta secretase. For example, structurally homologous molecules can contain deletions or additions of one or more contiguous or noncontiguous amino acids, such as a loop or a domain. Structurally homologous molecules also include "modified" human beta secretase molecules that have been chemically or enzymatically derivatized at one or more constituent amino acid, including side chain modifications, backbone modifications, and N- and C-terminal modifications including acetylation, hydroxylation, methylation, amidation, and the attachment of carbohydrate or lipid moieties, cofactors, and the like.

A heavy atom derivative of human beta secretase is also included as a human beta secretase homolog. The term "heavy atom derivative" refers to derivatives of human beta secretase produced by chemically modifying a crystal of human beta secretase. In practice, a crystal is soaked in a solution containing heavy metal atom salts, or organometallic compounds, e.g., lead chloride, gold thiomalate, thiomersal or uranyl acetate, which can diffuse through the crystal and bind to the surface of the protein. The location(s) of the bound heavy metal atom(s) can be determined by x-ray diffraction analysis of the soaked crystal. This information, in turn, is used to generate the phase information used to construct three-dimensional structure of the protein (T. L. Blundell and N. L. Johnson, *Protein Crystallography,* Academic Press (1976)).

Because human beta secretase can crystallize in more than one crystal form, the structure coordinates of human beta secretase as provided by this invention are particularly useful in solving the structure of other crystal forms of human beta secretase or human beta secretase complexes.

The structure coordinates of human beta secretase as provided by this invention are particularly useful in solving the structure of human beta secretase mutants. Mutants may be prepared, for example, by expression of human beta secretase cDNA previously altered in its coding sequence by oligonucleotide-directed mutagenesis. Mutants may also be generated by site-specific incorporation of unnatural amino acids into beta secretase proteins using the general biosynthetic method of Noren et al., *Science,* 244:182-88 (1989). In this method, the codon encoding the amino acid of interest in wild-type human beta secretase is replaced by a "blank" nonsense codon, TAG, using oligonucleotide-directed mutagenesis. A suppressor tRNA directed against this codon is then chemically aminoacylated in vitro with the desired unnatural amino acid. The aminoacylated tRNA is then added to an in vitro translation system to yield a mutant human beta secretase with the site-specific incorporated unnatural amino acid.

Selenocysteine or selenomethionine may be incorporated into wild-type or mutant human beta secretase by expression of human beta secretase-encoding cDNAs in auxotrophic *E. coli* strains (Hendrickson et al., *EMBO J.,* 9:1665-72 (1990)). In this method, the wild-type or mutagenized human beta secretase cDNA may be expressed in a host organism on a growth medium depleted of either natural cysteine or methionine (or both) but enriched in selenocysteine or selenomethionine (or both). Alternatively, selenomethionine analogues may be prepared by down regulation methionine biosynthesis. (Benson et al., *Nat. Struct. Biol.,* 2:644-53 (1995); Van Duyne et al., *J. Mol. Biol.,* 229:105-24 (1993)).

The structure coordinates of human beta secretase listed in Table 1 are also particularly useful to solve the structure of crystals of human beta secretase, human beta secretase mutants or human beta secretase homologs co-complexed with a variety of chemical entities. This approach enables the determination of the optimal sites for interaction between chemical entities, including candidate human beta secretase modifiers and human beta secretase. Potential sites for modification within the various binding sites of the molecule can also be identified. This information provides an additional tool for determining the most efficient binding interactions, for example, increased hydrophobic interactions, between human beta secretase and a chemical entity. For example, high resolution x-ray diffraction data collected from crystals exposed to different types of solvent allows the determination of where each type of solvent molecule resides. Small molecules that bind tightly to those sites can then be designed and synthesized and tested for their potential human beta secretase inhibition activity.

All of the complexes referred to above may be studied using well-known x-ray diffraction techniques and may be refined versus 1.5-3.5 Å resolution x-ray data to an R value of about 0.30 or less using computer software, such as X-PLOR (Yale University, 81992, distributed by Molecular Simulations, Inc.; see, e.g., Blundell & Johnson, supra; *Meth. Enzymol.*, Vol. 114 & 115, H. W. Wyckoff et al., eds., Academic Press (1985)). This information may thus be used to optimize known human beta secretase modifiers, and more importantly, to design new human beta secretase modifiers.

The invention also includes the unique three-dimensional configuration defined by a set of points defined by the structure coordinates for a molecule or molecular complex structurally homologous to human beta secretase as determined using the method of the present invention, structurally equivalent configurations, and magnetic storage media including such set of structure coordinates.

Further, the invention includes structurally homologous molecules as identified using the method of the invention.

Homology Modeling

Using homology modeling, a computer model of a human beta secretase homolog can be built or refined without crystallizing the homolog. First, a preliminary model of the human beta secretase homolog is created by sequence alignment with human beta secretase, secondary structure prediction, the screening of structural libraries, or any combination of those techniques. Computational software may be used to carry out the sequence alignments and the secondary structure predictions. Structural incoherences, e.g., structural fragments around insertions and deletions, can be modeled by screening a structural library for peptides of the desired length and with a suitable conformation. For prediction of the side chain conformation, a side chain rotamer library may be employed. If the human beta secretase homolog has been crystallized, the final homology model can be used to solve the crystal structure of the homolog by molecular replacement, as described above. Next, the preliminary model is subjected to energy minimization to yield an energy minimized model. The energy minimized model may contain regions where stereochemistry restraints are violated, in which case such regions are remodeled to obtain a final homology model. The homology model is positioned according to the results of molecular replacement, and subjected to further refinement including molecular dynamics calculations.

Rational Drug Design

Computational techniques can be used to screen, identify, select and/or design chemical entities capable of associating with human beta secretase or structurally homologous molecules. Knowledge of the structure coordinates for human beta secretase permits the design and/or identification of synthetic compounds and/or other molecules which have a shape complementary to the conformation of the human beta secretase binding site. In particular, computational techniques can be used to identify or design chemical entities, such as modifiers, agonists and antagonists, that associate with a human beta secretase binding pocket or an beta secretase-like binding pocket. Potential modifiers may bind to or interfere with all or a portion of an active site of human beta secretase, and can be competitive, non-competitive, or uncompetitive inhibitors; or interfere with dimerization by binding at the interface between the two monomers. Once identified and screened for biological activity, these inhibitors/agonists/antagonists may be used therapeutically or prophylactically to block human beta secretase activity and, thus, prevent the onset and/or further progression of Alzheimer's disease. Structure-activity data for analogues of ligands that bind to or interfere with human beta secretase or beta secretase-like binding pockets can also be obtained computationally.

The term "chemical entity," as used herein, refers to chemical compounds, complexes of two or more chemical compounds, and fragments of such compounds or complexes. Chemical entities that are determined to associate with human beta secretase are potential drug candidates. Data stored in a machine-readable storage medium that displays a graphical three-dimensional representation of the structure of human beta secretase or a structurally homologous molecule, as identified herein, or portions thereof may thus be advantageously used for drug discovery. The structure coordinates of the chemical entity are used to generate a three-dimensional image that can be computationally fit to the three-dimensional image of human beta secretase or a structurally homologous molecule. The three-dimensional molecular structure encoded by the data in the data storage medium can then be computationally evaluated for its ability to associate with chemical entities. When the molecular structures encoded by the data is displayed in a graphical three-dimensional representation on a computer screen, the protein structure can also be visually inspected for potential association with chemical entities.

One embodiment of the method of drug design involves evaluating the potential association of a known chemical entity with human beta secretase or a structurally homologous molecule, particularly with a human beta secretase binding pocket or beta secretase-like binding pocket. The method of drug design thus includes computationally evaluating the potential of a selected chemical entity to associate with any of the molecules or molecular complexes set forth above. This method includes the steps of (a) employing computational means to perform a fitting operation between the selected chemical entity and a binding pocket or a pocket nearby the binding pocket of the molecule or molecular complex; and (b) analyzing the results of said fitting operation to quantify the association between the chemical entity and the binding pocket.

In another embodiment, the method of drug design involves computer-assisted design of chemical entities that associate with human beta secretase, its homologs, or portions thereof. Chemical entities can be designed in a step-wise fashion, one fragment at a time, or may be designed as a whole or "de novo."

To be a viable drug candidate, the chemical entity identified or designed according to the method must be capable of structurally associating with at least part of a human beta secretase or beta secretase-like binding pockets, and must be able, sterically and energetically, to assume a conformation that allows it to associate with the human beta secretase or beta secretase-like binding pocket. Non-covalent molecular interactions important in this association include hydrogen bonding, van der Waals interactions, hydrophobic interactions, and electrostatic interactions. Conformational considerations include the overall three-dimensional structure and orientation of the chemical entity in relation to the binding pocket, and the spacing between various functional groups of an entity that directly interact with the beta secretase-like binding pocket or homologs thereof.

Optionally, the potential binding of a chemical entity to a human beta secretase or beta secretase-like binding pocket is analyzed using computer modeling techniques prior to the actual synthesis and testing of the chemical entity. If these computational experiments suggest insufficient interaction and association between it and the human beta secretase or beta secretase-like binding pocket, testing of the entity is obviated. However, if computer modeling indicates a strong interaction, the molecule may then be synthesized and tested for its ability to bind to or interfere with a human beta secretase or beta secretase-like binding pocket. Binding assays to determine if a compound (e.g., an inhibitor) actually interferes with human beta secretase can also be performed and are well known in the art. Binding assays may employ kinetic or thermodynamic methodology using a wide variety of techniques including, but not limited to, microcalorimetry, circular dichroism, capillary zone electrophoresis, nuclear magnetic resonance spectroscopy, fluorescence spectroscopy, and combinations thereof.

One method for determining whether a modifier binds to a protein is isothermal denaturation. This method includes taking a sample of a protein (in the presence or absence of substrates) at a fixed elevated temperature where denaturation of the protein occurs in a given time frame, adding the chemical entity to the protein, and monitoring the rate of denaturation. If the chemical entity does bind to the protein, it is expected that the rate of denaturation would be slower in the presence of the chemical entity than in the absence of the chemical entity. For example, this method has been described in Epps et al., *Anal. Biochem.*, 292:40-50 (2001).

One skilled in the art may use one of several methods to screen chemical entities or fragments for their ability to associate with a human beta secretase or beta secretase-like binding pocket. This process may begin by visual inspection of, for example, a human beta secretase or beta secretase-like binding pocket on the computer screen based on the human beta secretase structure coordinates listed in Table 1 or other coordinates which define a similar shape generated from the machine-readable storage medium. Selected fragments or chemical entities may then be positioned in a variety of orientations, or docked, within the binding pocket. Docking may be accomplished using software such as QUANTA and SYBYL, followed by energy minimization and molecular dynamics with standard molecular mechanics forcefields, such as CHARMM and AMBER.

Specialized computer programs may also assist in the process of selecting fragments or chemical entities. Examples include GRID (Goodford, *J. Med. Chem.*, 28:849-57 (1985); available from Oxford University, Oxford, UK); MCSS (Miranker et al., *Proteins: Struct. Funct. Gen.*, 11:29-34 (1991); available from Molecular Simulations, San Diego, Calif.); AUTODOCK (Goodsell et al., *Proteins: Struct. Funct. Genet.*, 8:195-202 (1990); available from Scripps Research Institute, La Jolla, Calif.); and DOCK (Kuntz et al., *J. Mol. Biol.*, 161:269-88 (1982); available from University of California, San Francisco, Calif.).

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of human beta secretase. This would be followed by manual model building using software such as QUANTA or SYBYL (Tripos Associates, St. Louis, Mo.).

Useful programs to aid one of skill in the art in connecting the individual chemical entities or fragments include, without limitation, CAVEAT (P. A. Bartlett et al., in "Molecular Recognition in Chemical and Biological Problems," Special Publ., Royal Chem. Soc., 78:182-96 (1989); Lauri et al., *J. Comput. Aided Mol. Des.*, 8:51-66 (1994); available from the University of California, Berkeley, Calif.); 3D database systems such as ISIS (available from MDL Information Systems, San Leandro, Calif.; reviewed in Martin, *J. Med. Chem.*, 35:2145-54 (1992)); and HOOK (Eisen et al., *Proteins: Struc., Funct., Genet.*, 19:199-221 (1994); available from Molecular Simulations, San Diego, Calif.).

Human beta secretase binding compounds may be designed "de novo" using either an empty binding site or optionally including some portion(s) of a known modifier(s). There are many de novo ligand design methods including, without limitation, LUDI (Bohm, *J. Comp. Aid. Molec. Design.*, 6:61-78 (1992); available from Molecular Simulations Inc., San Diego, Calif.); LEGEND (Nishibata et al., *Tetrahedron*, 47:8985 (1991); available from Molecular Simulations Inc., San Diego, Calif.); LeapFrog (available from Tripos Associates, St. Louis, Mo.); and SPROUT (Gillet et al., *J. Comput. Aided Mol. Design*, 7:127-53 (1993); available from the University of Leeds, UK).

Once a compound has been designed or selected by the above methods, the efficiency with which that entity may bind to or interfere with a human beta secretase or beta secretase-like binding pocket may be tested and optimized by computational evaluation. For example, an effective human beta secretase or beta secretase-like binding pocket modifier must preferably demonstrate a relatively small difference in energy between its bound and free states (i.e., a small deformation energy of binding). Thus, the most efficient human beta secretase or beta secretase-like binding pocket modifiers should preferably be designed with a deformation energy of binding of at most about 10 kcal/mole; more preferably, at most 7 kcal/mole. Human beta secretase or beta secretase-like binding pocket modifiers may interact with the binding pocket in more than one conformation that is similar in overall binding energy. In those cases, the deformation energy of binding is taken to be the difference between the energy of the free entity and the average energy of the conformations observed when the modifier binds to the protein.

An entity designed or selected as binding to or interfering with a human beta secretase or beta secretase-like binding pocket may be further computationally optimized so that in its bound state it would preferably lack repulsive electrostatic interaction with the target enzyme and with the surrounding water molecules. Such non-complementary electrostatic interactions include repulsive charge-charge, dipole-dipole, and charge-dipole interactions.

Specific computer software is available in the art to evaluate compound deformation energy and electrostatic interactions. Examples of programs designed for such uses include: Gaussian 94, revision C (M. J. Frisch, Gaussian, Inc., Pittsburgh, Pa. (1995)); AMBER, version 4.1 (P. A. Kollman, University of California at San Francisco, (1995)); QUANTA/CHARMM (Molecular Simulations, Inc., San Diego, Calif. (1995)); Insight II/Discover (Molecular Simulations, Inc., San Diego, Calif. (1995)); DelPhi (Molecular Simulations, Inc., San Diego, Calif. (1995)); and AMSOL (Quantum Chemistry Program Exchange, Indiana University). These programs may be implemented, for instance, using a Silicon Graphics workstation such as an Indigo with "IMPACT" graphics. Other hardware systems and software packages will be known to those skilled in the art.

Another approach encompassed by this invention is the computational screening of small molecule databases for chemical entities or compounds that can bind in whole, or in part, to a human beta secretase or beta secretase-like binding pocket. In this screening, the quality of fit of such entities to the binding site may be judged either by shape complementarity or by estimated interaction energy (Meng et al., *J. Comp. Chem.*, 13:505-24 (1992)).

This invention also enables the development of chemical entities that can isomerize to short-lived reaction intermediates in the chemical reaction of a substrate or other compound that interferes with or with human beta secretase. Time-dependent analysis of structural changes in human beta secretase during its interaction with other molecules is carried out. The reaction intermediates of human beta secretase can also be deduced from the reaction product in co-complex with human beta secretase. Such information is useful to design improved analogues of known human beta secretase modifiers or to design novel classes of potential modifiers based on the reaction intermediates of the human beta secretase and modifier co-complex. This provides a novel route for designing human beta secretase modifiers with both high specificity and stability.

Yet another approach to rational drug design involves probing the human beta secretase crystal of the invention with molecules including a variety of different functional groups to determine optimal sites for interaction between candidate human beta secretase modifiers and the protein. For example, high resolution x-ray diffraction data collected from crystals soaked in or co-crystallized with other molecules allows the determination of where each type of solvent molecule sticks. Molecules that bind tightly to those sites can then be further modified and synthesized and tested for their beta secretase modifier activity (Travis, *Science*, 262:1374 (1993)).

In a related approach, iterative drug design is used to identify modifiers of human beta secretase. Iterative drug design is a method for optimizing associations between a protein and a compound by determining and evaluating the three-dimensional structures of successive sets of protein/compound complexes. In iterative drug design, crystals of a series of protein/compound complexes are obtained and then the three-dimensional structures of each complex is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized.

A compound that is identified or designed as a result of any of these methods can be obtained (or synthesized) and tested for its biological activity, e.g., inhibition of beta secretase activity.

Pharmaceutical Compositions (Modifiers)

Pharmaceutical compositions of this invention include a potential modifier of human beta secretase activity identified according to the invention, or a pharmaceutically acceptable salt thereof, and a pharmaceutically acceptable carrier, adjuvant, or vehicle. The term "pharmaceutically acceptable carrier" refers to a carrier(s) that is "acceptable" in the sense of being compatible with the other ingredients of a composition and not deleterious to the recipient thereof. Optionally, the pH of the formulation is adjusted with pharmaceutically acceptable acids, bases, or buffers to enhance the stability of the formulated compound or its delivery form.

Methods of making and using such pharmaceutical compositions are also included in the invention. The pharmaceutical compositions of the invention can be administered orally, parenterally, by inhalation spray, topically, rectally, nasally, buccally, vaginally, or via an implanted reservoir. Oral administration or administration by injection is preferred. The term parenteral as used herein includes subcutaneous, intracutaneous, intravenous, intramuscular, intraarticular, intrasynovial, intrasternal, intrathecal, intralesional, and intracranial injection or infusion techniques.

Dosage levels of about 0.01 to about 100 mg/kg body weight per day, preferably of about 0.5 to about 75 mg/kg body weight per day of the human beta secretase inhibitory compounds described herein are useful for the prevention and treatment of human beta secretase mediated disease. Typically, the pharmaceutical compositions of this invention will be administered about 1 to about 5 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain about 5% to about 95% active compound (w/w). Preferably, such preparations contain about 20% to about 80% active compound.

In order that this invention be more fully understood, the following examples are set forth. These examples are for the purpose of illustration only and are not to be construed as limiting the scope of the invention in any way.

EXAMPLES

Example 1

Crystallization and Structure Determination of Human Beta Secretase in the C2 Crystal Form Examples of the crystallization and structure determination of human beta secretase in the C2 crystal form are disclosed in U.S. Provisional Application Ser. No. 60/334,648, filed Nov. 30, 2001 and U.S. patent application Ser. No. 10/143,723, filed May 10, 2002, and entitled "CRYSTALLIZATION AND STRUCTURE DETERMINATION OF BACE AND/OR BACE-LIKE PROTEINS".

Expression, Purification, and Crystallization

A BACE construct, pQE70-Met-Arg-Gly-Ser-Phe-Val-Glu- . . . . Thr-Asp-Glu-Ser-Arg-Ser-(His)$_6$ (see SEQ ID NO:1) referred to as PQE70-BACE was cloned and expressed as inclusion bodies. Inclusion bodies obtained from 40 liters of cell culture were washed one time in 700 ml of 10 mM TRIS buffer, pH 8.12, 1 mM EDTA (TE). The inclusion bodies were extracted with 400 ml 7.5 M urea, 100 mM AMPSO, 1 mM glycine, 1 mM EDTA, and 100 mM β-Mercaptoethanol (BME), pH 10.5-10.8. After centrifugation, the protein concentration of the supernatant was adjusted by dilution with the above buffer to read ~5.0 at $A_{280}$. The protein was then diluted with 7.5 M urea, 100 mM AMPST, 1 mM glycine, 1 mM EDTA, and the BME concentration adjusted to 10 mM by the addition of BME to read an $A_{280}$~0.5 and a pH=10.5-10.8. The solution was centrifuged. Analysis of the sample in 7.5 M urea by SDS-PAGE revealed BACE as the major component of the solubilized inclusion bodies. BACE migrated as a band of Mr~45,000. Refolding was carried out by a 20-25 fold dilution with cold water (4-15° C.). Upon dilution, the pH dropped automatically to 9.5-10.2. The sample was then allowed to rest in the cold room. Activity assays were performed daily to monitor protein refolding. Results from various experiments indicated that maximal activity was usually reached after 4-5 weeks.

Figure 2:
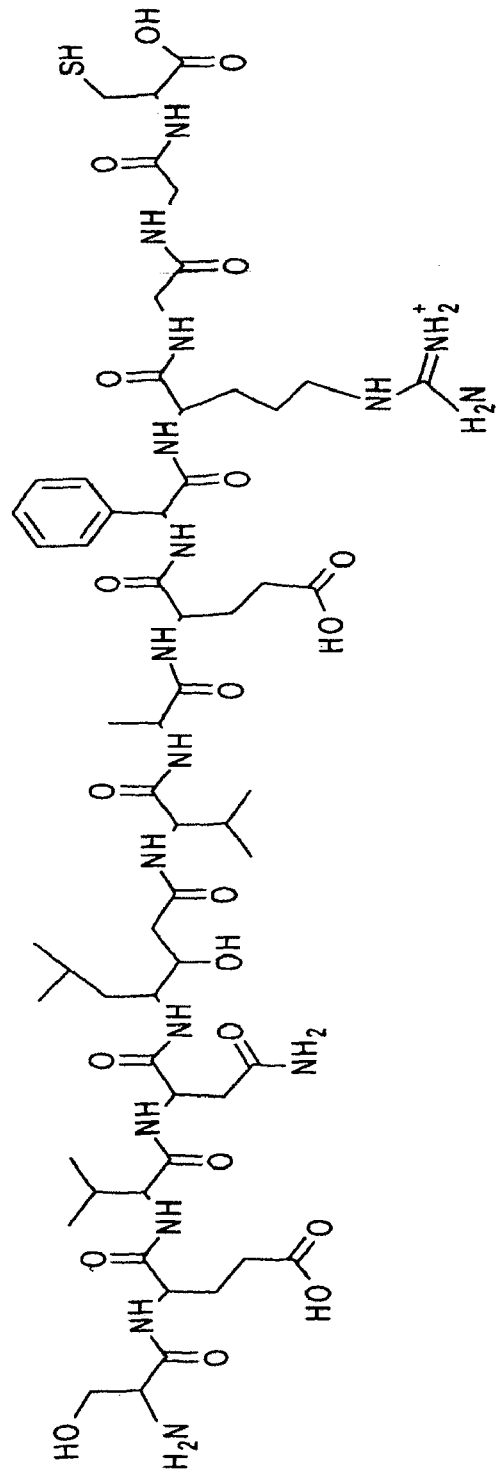
FIG. 2 is the synthetic peptide Ser-Glu-Val-Asn-Sta-Val-Ala-Glu-Phe-Arg-Gly-Gly-Cys (where Sta=statine) (SEQ ID NO:2) used for affinity purification of BACE.

Prior to purification, the pH of the refolded protein was lowered from about 10 to 8.5 with HCl. The solution was loaded onto three 50 ml Q-Sepharose columns (Pharmacia Biotech XK 50). The columns were pre-equilibrated in 0.4 M Urea, 10 mM AMPSO, pH 8.5. After refolded protein was loaded onto the columns, they were washed with 500 ml of 0.4 M Urea, 10 mM TRIS, pH 8.2, The columns were eluted with 180-245 ml of 0.75 M NaCl in 0.4 M Urea 10 mM TRIS buffer, pH 8.2. The eluates were then dialyzed versus 20 mM HEPES, pH 8.0. The samples were then removed from dialysis and dropped into 1 M NaMES, pH 5.7 (0.1 M final concentration). After centrifugation (20K×g) the supernatant was dropped into 1 M Na-acetate, 1 M NaMES, pH 5.0 (0.2 M Na-acetate, 0.28 M Na-MES was the final concentration). No precipitation was observed at this step. This solution was then applied to a 15 ml affinity column equilibrated at the same pH. The column was washed with 6 column volumes of 20 mM sodium acetate buffer pH 4.5, 150 mM NaCl. BACE was eluted at pH 8.5 using about 50 ml of 0.1 M borate buffer. The resin had been cross-linked with the synthetic peptide shown in FIG. 2. This final step removed any residual contaminants. From 40 liter of *E. coli* cell culture, the amount of protein obtained was 137 mg of highly purified pQE70-BACE construct. Purified pQE70-BACE was dialyzed into 100 mM NaBorate pH 8.5.

In an effort to reduce non-specific aggregation, the enzyme was concentrated in the presence of the inhibitor. The purpose of this was two-fold: First, the compound would bind active molecules forming a homogenous population, and second, the complex, once locked in place would then not be able to contribute to non-specific aggregation. The concentration of the stock protein solution was determined and multiplied by 2.4. This calculation provides the excess inhibitor to be added to the dilute protein sample before the concentration. The appropriate amount of 50 mM inhibitor stock solution (in 100% DMSO) was added, and the solution was incubated on ice 30 minutes before concentration. A 30K MWCO (Molecular Weight Cut-Off) Ultrafree-4 concentrator (Millipore, Bedford, Mass.) was pretreated with 2.0 ml of the following solution: 20 mM Hepes pH 7.8, 20% Glycerol, 5% PEG 8000, 0.1 M NaCl. The sample was spun at 3810 rpm (3000×g) in an SH-3000 rotor in 10 minute increments until desired volume is achieved. The membrane was rinsed with 2×1.0 ml 20 mM Hepes pH 7.8. The first aliquot of protein:compound mix was added to the concentrator and spun as above until ½ the volume remained. The concentrator was gently inverted to mix the protein and another aliquot was added. The above procedure was repeated until all of the unconcentrated protein:compound mix was in the concentrator. At this point, the sample was gently concentrated until a final volume was reached that yielded approx. 8-10 mg/ml concentration. This concentrated sample was used for co-crystallization studies. It was also determined that concentrating the protein in the absence of inhibitor to a concentration of 10-13 mg/ml and then subsequently adding inhibitor to the protein provided a protein sample that would crystallize albeit at a slower rate.

Sparse matrix screening of pQE70-BACE in the presence of the inhibitor shown in FIG. 1 at 20° C. in the hanging drop vapor diffusion method was performed with the commercially available Wizard I screen (Emerald Biostructures, Bainbridge Island, Wash.) and Hampton I screen (Hampton Research, Laguna Nigel, Calif.). A shower of microcrystals was observed in Wizard I screen condition 45 (20% PEG 3000 (precipitant), 0.1 M sodium acetate pH 4.5 (buffer)) and Hampton I screen condition 37 (8% PEG 4000 (precipitant), 0.1 M sodium acetate pH 4.6 (buffer)). First round optimization experiments, pQE70-BACE produced crystals in 0.1 M sodium acetate pH 4.5-5.6 (buffer) and PEG 2000, 3000, 4000, and 8000 (precipitants) at 20° C. Initial crystals grown in PEG 3000 consisted of rod clusters and single rod shaped crystals with a large depletion. A crystal grown in 16% PEG 3000 (precipitant) and 0.1 M sodium acetate pH 4.6 (buffer) at 20° C., with an approximate size of 0.6×0.15 mm, diffracted to 1.7 Å at the Argonne National Laboratory. The cryogenic solution for this crystal consisted of synthetic mother liquor based on the well solution and glycerol: 16% PEG 3000, 0.1 M sodium acetate pH 4.6, and 5-30% glycerol (cryoagent) in 5% increments. The cryogenic solutions were added stepwise in 5-minute increments with increasing percentages of glycerol. The crystal was looped out and flash frozen in liquid nitrogen. The crystal contains one molecule per asymmetric unit with cell dimensions of a=73.1 Å, b=105.1 Å, c=50.5 Å, α=90°, β=94.8°, γ90° in space group C2.

Second round optimization also resulted in large single crystals, with an approximate size of 0.3-0.4×0.12-0.2 mm, in 4-6% PEG 4000 and PEG 8000 (precipitants), 0.1 M sodium acetate pH 4.6-5.6 (buffers) at 20° C. The typical cryogenic solution for these crystals consisted of one percentage higher of the same PEG condition found in the well mother liquor of the crystal, 0.1 M sodium acetate (pH of the mother liquor), and 25% glycerol. The cryogenic solutions were added every 5 minutes with stepwise additions of 0.1 µl, 0.25 µl, 0.50 µl, 1.0 µl, and 2.0 µl. After a one hour soak, crystals were looped out and flash frozen in liquid nitrogen. These crystals have the same unit cell as the pET11a crystals (a=81 Å, b=103 Å, c=100 Å, α=γ=90, β=105°) with a space group of $P2_1$ and three molecules per asymmetric unit but diffracted to lower resolution (2.5-2.8 Å) than the C2 crystal form, discussed above.

Third round optimization revealed that the percentage of PEG (precipitant) was the critical component required to distinguish between the C2 and $P2_1$ crystal forms. The greater the percentage of precipitant present, the more dehydrated the crystals become resulting in higher resolution diffraction (the solvent content in the $P2_1$ crystals is 54% compared to the 42% solvent content for the C2 crystals). Crystallization in 8% PEG or less reproducibly gave the lower resolution $P2_1$ crystal form while crystallization in 16% PEG or more (up to 45% PEG) reproducibly gave the higher resolution C2 crystal form. Alternative PEGs such as PEG 200, PEG 350 MME, PEG 400, PEG 550 MME, PEG 750 MME, PEG 1000, PEG 2000, PEG 2000 MME, PEG 3000, PEG 4000, PEG 8000 also produce suitable crystals when used with pQE70-BACE. The buffer for crystallizing with the different forms of PEG was 0.1 M sodium acetate pH 4.6-5.6 at a temperature of 20° C. No additional salt was required for crystallization. In addition, streak seeding at the stage of setting up the hanging drops aided crystal growth. A range of protein concentration from 2 mg/ml to 13 mg/ml has proven useful in preparing crystals.

X-Ray Diffraction Characterization

Initial data collection was carried out on home source X-rays using a Rigaku RUH3R X-ray generator (with osmic confocal mirros) and a R-axis IV ++detector (Molecular Structure Corporation, The Woodlands, Tex). Initial analysis of the crystals revealed 1.9 Å diffraction on the home source. The same crystal was refrozen and transported to the synchrotron for subsequent data collection at the Advanced Photon Source (Argonne, Ill.) at beamline 17-ID. Using synchrotron radiation, the crystal diffracted to 1.7 Å resolution. Crystals were of the space group C2 with cell dimensions of a=73.1 Å, b=105.1 Å, c=50.5 Å, α=90°, β=94.8°, γ=90°. The Matthews coefficient for these crystals assuming that there is one molecule in the asymmetric unit is 2.1 Å/Da with 42% solvent. The structure determination (see below) revealed the presence of electron density in the active site appropriate for the inhibitor shown in FIG. 1.

Molecular Replacement

The structure was solved by molecular replacement. A solution was determined using AMORE (Navaza, *Acta Cryst.*, D50:157-63 (1994); Collaborative Computational Project N4, *Acta Cryst.* D50:760-3 (1994)) by utilizing a previously solved structure of human BACE produced in *E. coli* from the pET11a vector. The initial rotation solution gave a single strong peaks of 16.9σ. A translation search in space group C2 resulted in a correlation coefficient of 57.2 with an R-factor of 38.3% to 4 Å resolution. The high correlation coefficient and low R-factor suggested that the entire protein contents of the unit cell had been correctly identified; therefore, the search for additional molecules was abandoned.

TABLE 6

Data collection statistics for 1.9Å resolution data set of Human BACE derived from *E. coli* pQE70-BACE (C2 crystal form) produced protein used for refinement (data collected at λ 1.54 Å on home source X-rays). Data was processed with D*trek.

Rmerge vs Resolution

| Resolution range | Average counts | Num obs | Num rejs | Num ovlps | Num mults | $<<I>/<sig>>$ | ChiSq norm | Rmerge shell | Rmerge cumul |
|---|---|---|---|---|---|---|---|---|---|
| 19.97-4.08 | 33303 | 11727 | 46 | 11666 | 2975 | 10.3 | 0.35 | 0.039 | 0.039 |
| 4.08-3.25 | 27063 | 11593 | 43 | 11536 | 2913 | 9.6 | 0.48 | 0.048 | 0.043 |
| 3.25-2.84 | 11447 | 11354 | 44 | 11298 | 2839 | 8.1 | 0.75 | 0.066 | 0.047 |
| 2.84-2.58 | 6285 | 11441 | 77 | 11343 | 2852 | 6.8 | 0.99 | 0.080 | 0.049 |
| 2.58-2.39 | 4188 | 11239 | 98 | 11112 | 2785 | 5.8 | 1.22 | 0.097 | 0.052 |
| 2.39-2.25 | 3250 | 11130 | 123 | 10975 | 2753 | 5.1 | 1.30 | 0.111 | 0.054 |
| 2.25-2.14 | 2298 | 11102 | 164 | 10893 | 2732 | 4.4 | 1.40 | 0.131 | 0.056 |
| 2.14-2.05 | 1621 | 9532 | 111 | 9355 | 2350 | 3.7 | 1.41 | 0.149 | 0.057 |
| 2.05-1.97 | 1278 | 6190 | 95 | 6012 | 1527 | 3.6 | 1.26 | 0.147 | 0.058 |
| 1.97-1.90 | 798 | 4131 | 47 | 4004 | 1026 | 3.1 | 1.16 | 0.174 | 0.058 |
| 19.97-1.90 | 10512 | 99439 | 848 | 98194 | 24752 | 6.5 | 1.00 | 0.058 | 0.058 |

Redundancy vs Resolution

| Resolution range | Calc unique | Percent of reflections measured N times, N = | | | | | | | | % Comp shell | % Comp cumul |
|---|---|---|---|---|---|---|---|---|---|---|---|
| | | 0 | 1 | 2 | 3 | 4 | 5-8 | 9-12 | >12 | | |
| 19.97-4.08 | 3039 | 1.6 | 0.5 | 5.3 | 0.6 | 88.5 | 3.5 | 0.0 | 0.0 | 98.4 | 98.4 |
| 4.08-3.25 | 3011 | 2.8 | 0.5 | 3.2 | 0.8 | 89.5 | 3.3 | 0.0 | 0.0 | 97.2 | 97.8 |
| 3.25-2.84 | 2964 | 3.8 | 0.4 | 2.4 | 0.6 | 89.3 | 3.3 | 0.0 | 0.0 | 96.2 | 97.3 |
| 2.84-2.58 | 3013 | 4.6 | 0.7 | 2.3 | 0.5 | 88.4 | 3.3 | 0.0 | 0.0 | 95.4 | 96.8 |
| 2.58-2.39 | 2974 | 5.4 | 1.0 | 2.0 | 0.7 | 87.2 | 3.8 | 0.0 | 0.0 | 94.6 | 96.4 |
| 2.39-2.25 | 2963 | 6.0 | 1.1 | 2.1 | 0.7 | 86.4 | 3.7 | 0.0 | 0.0 | 94.0 | 96.0 |
| 2.25-2.14 | 2974 | 6.6 | 1.5 | 2.1 | 0.7 | 85.4 | 3.7 | 0.0 | 0.0 | 93.4 | 95.6 |
| 2.14-2.05 | 2986 | 19.1 | 2.2 | 1.4 | 1.6 | 72.7 | 2.9 | 0.0 | 0.0 | 80.9 | 93.8 |
| 2.05-1.97 | 2985 | 46.1 | 2.8 | 1.7 | 2.0 | 45.2 | 2.2 | 0.0 | 0.0 | 53.9 | 89.3 |
| 1.97-1.90 | 2978 | 62.9 | 2.7 | 1.2 | 2.2 | 29.9 | 1.2 | 0.0 | 0.0 | 37.1 | 84.1 |
| 19.97-1.90 | 29887 | 15.9 | 1.3 | 2.4 | 1.0 | 76.3 | 3.1 | 0.0 | 0.0 | 84.1 | 84.1 |

| Resolution range | Percent of reflections measured AT LEAST N times, N = | | | | | | |
|---|---|---|---|---|---|---|---|
| | 13 | 9 | 5 | 4 | 3 | 2 | 1 |
| 19.97-1.90 | 0.0 | 0.0 | 3.1 | 79.4 | 80.4 | 82.8 | 84.1 |

TABLE 7

Data collection statistics for 1.7 A resolution dataset of Human BACE derived from *E. coli* pQE70-BACE (C2 crystal form) produced protein used for the intial molecular replacement solution (data collected at λ 1.0000 Å at APS, 17-ID). Data was processed with HKL2000.

Summary of reflections intensities and R-factors by shells
R linear = SUM ( ABS(I − <I>)) / SUM (I)
R square = SUM ( (I − <I>)  2) / SUM (I  2)
Chi2 = SUM ( (I − <I>)  2) / (Error ** 2 * N / (N − 1) ) )
In all sums single measurements are excluded

| Shell limit | Lower Angstrom | Upper I | Average error | Average stat. | Norm. Chi**2 | Linear R-fac | Square R-fac |
|---|---|---|---|---|---|---|---|
| 50.00 | 3.66 | 37330.4 | 701.7 | 364.7 | 2.455 | 0.039 | 0.045 |
| 3.66 | 2.91 | 18841.1 | 418.8 | 278.7 | 2.645 | 0.054 | 0.059 |
| 2.91 | 2.54 | 7573.0 | 231.6 | 188.0 | 2.262 | 0.069 | 0.074 |
| 2.54 | 2.31 | 4744.8 | 196.2 | 174.2 | 1.911 | 0.085 | 0.088 |
| 2.31 | 2.14 | 3766.7 | 199.8 | 185.1 | 1.655 | 0.097 | 0.099 |
| 2.14 | 2.02 | 2682.2 | 195.6 | 186.9 | 1.324 | 0.115 | 0.110 |

TABLE 7-continued

Data collection statistics for 1.7 Å resolution dataset of Human BACE derived from
E. coli pQE70-BACE (C2 crystal form) produced protein used for the intial molecular
replacement solution (data collected at λ 1.0000 Å at APS, 17-ID). Data was
processed with HKL2000.

| | | | | | | | |
|---|---|---|---|---|---|---|---|
| 2.02 | 1.91 | 1738.0 | 182.7 | 178.3 | 1.079 | 0.143 | 0.131 |
| 1.91 | 1.83 | 1038.1 | 170.3 | 168.2 | 0.833 | 0.183 | 0.159 |
| 1.83 | 1.76 | 665.1 | 166.9 | 165.9 | 0.691 | 0.235 | 0.200 |
| 1.76 | 1.70 | 625.6 | 219.6 | 219.0 | 0.606 | 0.220 | 0.205 |
| All reflections | | 8296.7 | 272.2 | 211.6 | 1.651 | 0.060 | 0.052 |

| Shell | | I/Sigma in resolution shells: | | | | | | | |
|---|---|---|---|---|---|---|---|---|---|
| Lower | Upper | % of of reflections with I / Sigma less than | | | | | | | |
| limit | limit | 0 | 1 | 2 | 3 | 5 | 10 | 20 | >20 | total |
| 50.00 | 3.66 | 0.1 | 0.3 | 0.5 | 0.6 | 0.7 | 1.7 | 4.2 | 93.9 | 98.0 |
| 3.66 | 2.91 | 0.4 | 0.9 | 1.4 | 2.1 | 3.6 | 7.3 | 16.0 | 82.5 | 98.6 |
| 2.91 | 2.54 | 1.0 | 2.4 | 3.8 | 5.4 | 8.0 | 16.1 | 34.0 | 64.0 | 98.0 |
| 2.54 | 2.31 | 1.6 | 3.7 | 6.8 | 9.4 | 15.0 | 27.8 | 51.2 | 46.5 | 97.7 |
| 2.31 | 2.14 | 2.2 | 5.6 | 9.0 | 12.7 | 20.3 | 36.3 | 62.3 | 34.8 | 97.1 |
| 2.14 | 2.02 | 2.3 | 8.1 | 14.3 | 19.6 | 29.6 | 49.6 | 75.4 | 21.3 | 96.7 |
| 2.02 | 1.91 | 4.0 | 12.6 | 20.9 | 28.6 | 42.2 | 63.5 | 84.6 | 11.7 | 96.3 |
| 1.91 | 1.83 | 6.8 | 20.8 | 32.8 | 42.2 | 56.1 | 75.9 | 89.9 | 5.4 | 95.3 |
| 1.83 | 1.76 | 7.6 | 25.7 | 40.6 | 51.6 | 64.0 | 80.2 | 88.7 | 2.0 | 90.6 |
| 1.76 | 1.70 | 5.5 | 19.7 | 33.2 | 43.6 | 54.5 | 64.1 | 67.7 | 0.3 | 68.0 |
| All hkl | | 3.1 | 10.0 | 16.3 | 21.5 | 29.3 | 42.2 | 57.3 | 36.4 | 93.7 |

Model Building and Refinement

Further rigid body refinement of the model in CNX (Molecular Simulations, Inc) followed by minimization refinement gave an R-factor of 37.5% and a Free R-factor of 40.1% to 4.0 Å with an overall B-factor of 25.0 Å$^2$. Minimization and B-factor refinement led to a R-factor of 30.7% and a Free R-factor of 33.4%. The subsequent availability of a higher resolution data set to 1.7 Å afforded the opportunity to continue the high resolution refinement of the structure. The refinement against higher resolution data was initiated with a rigid body refinement followed by minimization and B-factor refinement leading to a R-factor of 29.6% and a Free R-factor of 30.7%. Including a round of simulated annealing refinement (A. T. Brunger, A. Krukowski, J. W. Erickson *Acta Cryst A* 46:585-93, (1990)) and minimization led to an improved R-factor of 26.3% and a Free R-factor of 28.3%. During each cycle of refinement a bulk solvent correction was incorporated (J. S. Jiang & A. T. Brunger, *J. Mol. Biol.* 243:100-15 (1994)). Progress of the refinement was monitored by a decrease in both the R-factor and Free R-factor.

At this point, inspection of the electron density map within the active site revealed electron density that was unaccounted for by the protein model and consistent with the shape of the inhibitor shown in FIG. 1 that was present in the crystallization conditions. Model building was done using the program CHAIN (J. S. Sack, *Journal of Molecular Graphics* 6:224-5 (1988)) and LORE (B. C. Finzel, *Meth. Enzymol.* 277:230-42 (1997)). Rebuilding of the model and the addition of water molecules into the model using the 1.7 Å resolution map afforded the opportunity for further cycles of refinement (including the inhibitor) giving improvement of the R-factor to 20.6% and a Free R-factor of 23.1%. The model includes three residues from the N terminal pro-region (61P-63P), residues 1-157, 165-309, 317-386. Loops for residues 158-164 and 310-316 were disordered in the electron density and therefore have been omitted from the model.

TABLE 8

Refinement Statistics for structure of Human BACE from pQE70 (C2 crystal form).

| | R-factor | Free R-factor | No. of reflections |
|---|---|---|---|
| 20-1.70 Å F ≧ 2σ | 0.206 | 0.231 | 37857 |

| | Bonds (Å) | Angles (°) |
|---|---|---|
| r.m.s deviation from ideal geometry | 0.006 | 1.4 |

| | Number of atoms | Average B-factor |
|---|---|---|
| Protein | 2982 | 24.6 |
| Waters | 370 | 35.5 |
| Ligand | 41 | 18.7 |
| Total | 3393 | 25.8 |

Example 2

Crystallization and Structure Determination of Human Beta Secretase in the C222$_1$ Crystal Form Expression, Purification, and Crystallization A BACE construct, pQE70-Met-Arg-Gly-Ser-Phe-Val-Glu- . . . . Thr-Asp-Glu-Ser-Arg-Ser-(His)$_6$ (see SEQ ID NO:1) referred to as PQE70-BACE was cloned and expressed as inclusion bodies. Inclusion bodies obtained from 40 liters of cell culture were washed one time in 700 ml of 10 mM TRIS buffer, pH 8.12, 1 mM EDTA (TE). The inclusion bodies were extracted with 400 ml 7.5 M urea, 100 mM AMPSO, 1 mM glycine, 1 mM EDTA, and 100 mM β-Mercaptoethanol (BME), pH 10.5-10.8. After centrifugation, the protein concentration of the supernatant was adjusted by dilution with the above buffer to read ~5.0 at A$_{280}$. The protein was then diluted with 7.5 M urea, 100 mM AMPST, 1 mM glycine, 1 mM EDTA, and the BME concentration adjusted to 10 mM by the addition of BME to read an $A_{280}$~0.5 and a pH=10.5-10.8. The solution was centrifuged. Analysis of the sample in 7.5 M urea by SDS-PAGE revealed BACE as the major component of the solubilized inclusion bodies. BACE migrated as a band of Mr~45,000. Refolding was carried out by a 20-25 fold dilution with cold water (4-15° C.). Upon dilution, the pH dropped automatically to 9.5-10.2. The sample was then allowed to rest in the cold room. Activity assays were performed daily to monitor protein refolding. Results from various experiments indicated that maximal activity was usually reached after 4-5 weeks.

Prior to purification, the pH of the refolded protein was lowered from about 10 to 8.5 with HCl. The solution was loaded onto three 50 ml Q-Sepharose columns (Pharmacia Biotech XK 50). The columns were pre-equilibrated in 0.4 M Urea, 10 mM AMPSO, pH 8.5. After refolded protein was loaded onto the columns, they were washed with 500 ml of 0.4 M Urea, 10 mM TRIS, pH 8.2. The columns were eluted with 180-245 ml of 0.75 M NaCl in 0.4 M Urea 10 mM TRIS buffer, pH 8.2. The eluates were then dialyzed versus 20 mM HEPES, pH 8.0. The samples were then removed from dialysis and dropped into 1 M NaMES, pH 5.7 (0.1 M final concentration). After centrifugation (20 K×g) the supernatant was dropped into 1 M Na-acetate, 1 M NaMES, pH 5.0 (0.2 M Na-acetate, 0.28 M Na-MES was the final concentration). No precipitation was observed at this step. This solution was then applied to a 15 ml affinity column equilibrated at the same pH. The column was washed with 6 column volumes of 20 mM sodium acetate buffer pH 4.5, 150 mM NaCl. BACE was eluted at pH 8.5 using about 50 ml of 0.1 M borate buffer. The resin had been cross-linked with synthetic peptide shown in FIG. 2. This final step removed any residual contaminants. From 40 liter of *E. coli* cell culture, the amount of protein obtained was 137 mg of highly purified pQE70-BACE construct. Purified pQE70-BACE was dialyzed into 100 mM NaBorate pH 8.5.

Crystallization Conditions for Unliganded BACE. Exploration of the optimal PEG conditions for growth of *E. coli* pQE70 BACE-1 co-crystals led to identification of a crystal structure of pQE70 without ligands (e.g., modifiers or inhibitors) bound to the active site. In an effort to repeat the concentration and conditions originally used to obtain the unliganded BACE-1 crystals, the molarity of the dilute protein sample was calculated in order to determine the amount of excess ligand (2.4× in 100% DMSO) that usually would have been added. The protein was incubated on ice with 2.4 excess of 100% DMSO for one hour. An Ultrafree-4 30,000 molecular weight cutoff centrifugal filter and tube (Millipore, Bedford, Mass.) was rinsed with 2.5 ml prep buffer consisting of 20 mM HEPES, pH 7.8, 20% glycerol, 5% PEG 8000, and 0.1 M sodium chloride. After incubation, the protein was added to the centricon and spun at 3500 rpm with a SH-3000 rotor at 5 minute intervals until the desired volume that provided a 6-8 mg/ml sample was reached.

Further experimentation demonstrated that concentration of pQE70 in the presence of DMSO as well as addition of DMSO to concentrated protein results in crystal growth in less than a week. It was also determined that streak seeding was preferred for crystal growth. A cat whisker was used to seed at setup with a thousand fold dilution of seed stock. The crystallization conditions were in the range of 24-39% PEG 200 and sodium acetate pH 5.0-5.6. The crystal morphology included single rods with an approximate size of 0.25×0.15 mm. The crystals were looped directly from the drop and flash frozen in liquid nitrogen. A crystal was diffracted to 1.75 Å at the Argonne National Laboratory. The crystal contained one molecule per asymmetric unit with cell dimensions of a=75, b=104, c=100, and $\alpha=\gamma\beta=90°$ in space group is $C222_1$.

Soaking Protocol to Produce Liganded BACE Crystals

Soaking experiments were performed using pQE70 crystals that were at least 0.15×0.1×0.05 mm. The well conditions for crystallization trays set up for soaking experiments consisted of 30% PEG 200, 100 mM sodium acetate pH 5.4 or 5.6. Ligand stabilization solution consisted of 33% PEG 200, 50 mM sodium acetate, pH 5.6, 50 mM sodium borate, pH 8.5, and 1-10 mM compound. The soaking solution was added over a two-hour period. After overnight incubation at 20° C., the crystals were looped out of the drop since both the growth and stabilization solution conditions were cryogenic.

Figure 7:
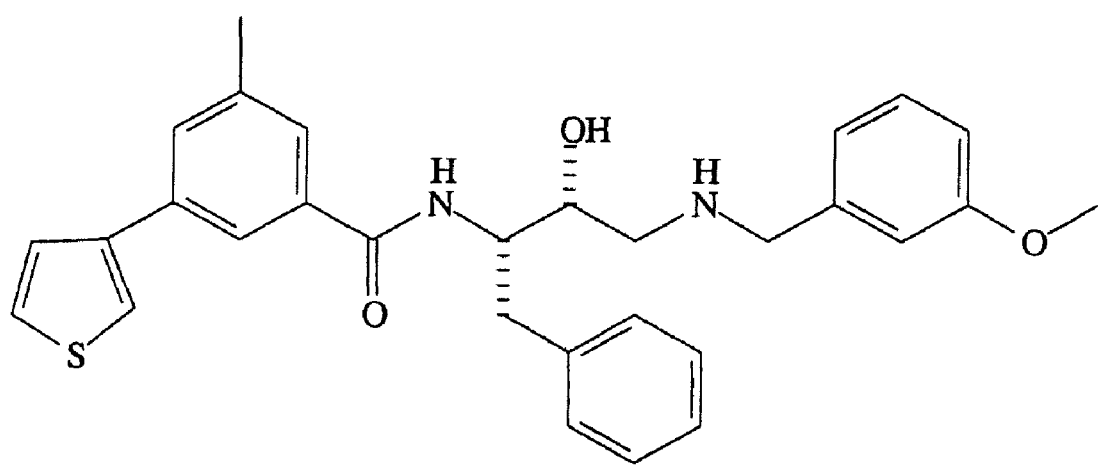
FIG. 7 is an illustration of the chemical structure of an inhibitor used in a soaking experiment.

Specifically, soaking experiments using the inhibitor shown in FIG. 1 ($IC_{50}$=1 nM) and the inhibitor shown in FIG. 7 ($IC_{50}$=8.8 µM) were used to define the preferred parameters for soaking inhibitors into unliganded pQE70 crystals. Using the data from experiments with the figure shown in FIG. 1, it was determined that a 2 mM overnight soak would be sufficient for high potency inhibitors ($IC_{50}$<100 nM). Using data from experiments with the inhibitor shown in FIG. 7, it was determined that a 5 mM overnight soak would provide a protein-inhibitor complex with moderate to low potency inhibitors ($IC_{50}$>100 nM).

However, some ligands may not successfully be soaked into unliganded crystals using these parameters. For such cases, the soak would be repeated using a higher concentration of ligand. If soaking under these conditions does not provide a protein-ligand complex, co-crystallization of a ligand with the pQE70 construct may be used to provide the protein-ligand complex.

X-Ray Diffraction Characterization

The initial crystals diffracted to 1.75 Å using synchrotron radiation at the Advanced Photon Source (Argonne, Ill.) at beamline 17-ID (operated by the Industrial Macromolecular Crystallography Consortium). Crystals were of the space group $C222_1$ with cell dimensions of a=75.0 Å, b=104.0 Å, c=100.4 Å, $\alpha=\beta=\gamma=90°$. The Matthews coefficient for these crystals, assuming that there is one molecule in the asymmetric unit, is 2.1 Å/Da with 42% solvent.

Molecular Replacement

The structure was solved by molecular replacement. A solution was determined using AMORE (Navaza, *Acta Cryst.*, D50:157-63 (1994); Collaborative Computational Project N4, *Acta Cryst.* D50:760-3 (1994)) by utilizing the coordinates from the structure of BACE in the C2 crystal form. The initial rotation solution gave a single strong peak of 11.5σ. A translation search in space group $C222_1$ resulted in a correlation coefficient of 59.2 with an R-factor of 38.1%. Further refinement of this solution in AMORE resulted in a correlation coefficient of 64.8 with an R-factor of 35.2% to 4 Å resolution. The high correlation coefficient and low R-factor suggested that the entire protein contents of the unit cell had been correctly identified; therefore, the search for additional molecules was abandoned.

TABLE 9

Data collection statistics for structure of unliganded E. coli
produced BACE (pQE70 construct)

Summary of reflections intensities and R-factors by shells

R linear = SUM (ABS(I − <I>))/SUM (I)
R square = SUM ((I − <I>)  2)/SUM (I  2)
Chi2 = SUM ((I − <I>)  2)/(Error ** 2 * N/(N − 1)))
In all sums single measurements are excluded

| Shell limit | | Average | Average | | Norm. | Linear | Square |
|---|---|---|---|---|---|---|---|
| Lower | Upper | | | | | | |
| Angstrom | | I | error | stat. | Chi**2 | R-fac | R-fac |
| 50.00 | 3.77 | 9478.7 | 153.1 | 90.7 | 1.401 | 0.035 | 0.043 |
| 3.77 | 2.99 | 5425.8 | 99.8 | 70.2 | 1.133 | 0.039 | 0.045 |
| 2.99 | 2.61 | 2491.1 | 53.6 | 42.5 | 0.935 | 0.044 | 0.049 |
| 2.61 | 2.38 | 1530.8 | 41.7 | 36.0 | 0.782 | 0.051 | 0.054 |
| 2.38 | 2.20 | 1238.1 | 44.3 | 40.1 | 0.757 | 0.061 | 0.062 |
| 2.20 | 2.07 | 967.7 | 41.6 | 38.8 | 0.845 | 0.087 | 0.091 |
| 2.07 | 1.97 | 743.9 | 42.1 | 40.1 | 0.856 | 0.120 | 0.125 |
| 1.97 | 1.89 | 1552.1 | 93.9 | 89.0 | 1.683 | 0.170 | 0.177 |
| 1.89 | 1.81 | 283.4 | 45.4 | 44.9 | 0.632 | 0.244 | 0.222 |
| 1.81 | 1.75 | 266.5 | 78.0 | 77.6 | 0.728 | 0.244 | 0.263 |
| All reflections | | 2487.4 | 68.0 | 54.9 | 0.950 | 0.051 | 0.048 |

| Shell | | I/Sigma in resolution shells: % of of reflections with I/Sigma less than | | | | | | | | |
|---|---|---|---|---|---|---|---|---|---|---|
| Lower limit | Upper limit | 0 | 1 | 2 | 3 | 5 | 10 | 20 | >20 | total |
| 50.00 | 3.77 | 0.9 | 1.6 | 1.7 | 1.9 | 2.5 | 3.9 | 6.5 | 84.3 | 90.8 |
| 3.77 | 2.99 | 0.5 | 1.0 | 1.3 | 1.8 | 2.8 | 4.9 | 9.9 | 71.2 | 81.1 |
| 2.99 | 2.61 | 0.4 | 1.3 | 2.2 | 3.2 | 5.1 | 10.5 | 21.4 | 78.6 | 100.0 |
| 2.61 | 2.38 | 1.0 | 2.5 | 4.0 | 5.3 | 8.6 | 16.2 | 31.4 | 68.6 | 100.0 |
| 2.38 | 2.20 | 2.3 | 3.2 | 4.2 | 5.2 | 7.3 | 11.8 | 20.3 | 26.9 | 47.2 |
| 2.20 | 2.07 | 2.7 | 5.4 | 8.9 | 11.9 | 17.9 | 30.6 | 55.4 | 44.6 | 100.0 |
| 2.07 | 1.97 | 1.8 | 6.1 | 10.3 | 14.8 | 22.6 | 41.3 | 69.3 | 30.7 | 100.0 |
| 1.97 | 1.89 | 7.3 | 9.0 | 10.5 | 12.0 | 14.6 | 20.4 | 31.7 | 12.2 | 43.9 |
| 1.89 | 1.81 | 11.7 | 21.9 | 31.2 | 39.5 | 54.2 | 76.7 | 94.2 | 4.7 | 98.9 |
| 1.81 | 1.75 | 3.9 | 16.4 | 31.3 | 43.3 | 59.1 | 72.5 | 78.3 | 0.7 | 79.0 |
| All hkl | | 3.2 | 6.8 | 10.5 | 13.8 | 19.3 | 28.7 | 41.5 | 42.7 | 84.2 |

| Shell | | Summary of observation redundancies: | | | | | | | | |
|---|---|---|---|---|---|---|---|---|---|---|
| Lower | Upper | % of reflections with given No. of observations | | | | | | | | |
| limit | limit | 0 | 1 | 2 | 3 | 4 | 5-6 | 7-8 | 9-12 | 13-19 | >19 | total |
| 50.00 | 3.77 | 9.2 | 2.0 | 2.6 | 3.4 | 11.2 | 10.0 | 61.6 | 0.0 | 0.0 | 0.0 | 90.8 |
| 3.77 | 2.99 | 18.9 | 1.0 | 1.0 | 2.3 | 6.5 | 10.7 | 59.5 | 0.0 | 0.0 | 0.0 | 81.1 |
| 2.99 | 2.61 | 0.0 | 0.1 | 0.4 | 1.9 | 6.4 | 13.6 | 77.6 | 0.0 | 0.0 | 0.0 | 100.0 |
| 2.61 | 2.38 | 0.0 | 0.0 | 0.3 | 1.6 | 6.0 | 15.0 | 77.0 | 0.0 | 0.0 | 0.0 | 100.0 |
| 2.38 | 2.20 | 52.8 | 1.2 | 0.8 | 1.3 | 3.0 | 7.9 | 33.1 | 0.0 | 0.0 | 0.0 | 47.2 |
| 2.20 | 2.07 | 0.0 | 0.2 | 0.3 | 1.9 | 5.5 | 18.4 | 73.7 | 0.0 | 0.0 | 0.0 | 100.0 |
| 2.07 | 1.97 | 0.0 | 0.0 | 0.3 | 1.1 | 5.5 | 19.5 | 73.4 | 0.2 | 0.0 | 0.0 | 100.0 |
| 1.97 | 1.89 | 56.1 | 2.0 | 2.4 | 4.3 | 5.5 | 10.1 | 19.5 | 0.1 | 0.0 | 0.0 | 43.9 |
| 1.89 | 1.81 | 1.1 | 1.5 | 2.7 | 5.3 | 9.6 | 34.2 | 45.1 | 0.5 | 0.0 | 0.0 | 98.9 |
| 1.81 | 1.75 | 21.0 | 17.8 | 21.3 | 14.7 | 11.6 | 10.9 | 2.6 | 0.0 | 0.0 | 0.0 | 79.0 |
| All hkl | | 15.8 | 2.5 | 3.2 | 3.8 | 7.1 | 15.0 | 52.5 | 0.1 | 0.0 | 0.0 | 84.2 |

Model Building and Refinement

Further rigid body refinement of the model in CNX (Accerlys, Inc, www.accerlys.com) followed by minimization refinement gave an R-factor of 42.9% and a Free R-factor of 43.1% to 4.0 Å with an overall B-factor of 25.0 Å$^2$. Minimization and B-factor refinement led to a R-factor of 32.7% and a Free R-factor of 35.1%. During each cycle of refinement a bulk solvent correction was incorporated (Jiang et al., *J. Mol. Biol.*, 243:100-15 (1994)). Progress of the refinement was monitored by a decrease in both the R-factor and Free R-factor. Inspection of the active site at this stage revealed the absence of any inhibitor electron density and the movement of flap residues 66-76 suggested that a ligand-free form of the enzyme had been obtained. Model building was done using the program CHAIN (Sack, *Journal of Molecular Graphics*, 6:224-25 (1988)) and LORE (Finzel, *Meth. Enzymol.*, 277: 230-42 (1997)). The electron density for the main chain of the active site flap was fairly well resolved, although the electron density for the side chains of these residues was usually disordered. Further cycles of refinement led to improvement of the R-factor to 23.3% and a Free R-factor of 26.8%. Residues 158-163 were disordered in the electron density and therefore have been omitted from the model. Further details of the refinement are shown in Table 10.

TABLE 10

Refinement Statistics for structure of unliganded *E. coli* produced BACE (pQE70 construct)

|  | R-factor | Free R-factor | No. of reflections |
|---|---|---|---|
| 20-1.75 Å F ≧ 2σ | 0.234 | 0.268 | 33362 |

|  | Bonds (Å) | Angles (°) |
|---|---|---|
| r.m.s deviation from ideal geometry | 0.006 | 1.6 |

|  | Number of atoms | Average B-factor |
|---|---|---|
| Protein | 3132 | 23.6 |
| Waters | 205 | 28.7 |
| Total | 3337 | 23.9 |

The complete disclosure of all patents, patent applications including provisional applications, and publications, and electronically available material (e.g., GenBank amino acid and nucleotide sequence submissions; and protein data bank (pdb) submissions) cited herein are incorporated by reference. The foregoing detailed description and examples have been given for clarity of understanding only. No unnecessary limitations are to be understood therefrom. The invention is not limited to the exact details shown and described; many variations will be apparent to one skilled in the art and are intended to be included within the invention defined by the claims.

Sequence Listing Free Text

SEQ ID NO:1 residues for the *E. coli* expressed recombinant human beta secretase SEQ ID NO:2 synthetic peptide

---

What is claimed is:

1. A method of identifying the ability for a potential ligand to bind to Beta Amyloid Cleaving Enzyme (BACE), the method comprising:
exposing a crystal of an unliganded BACE polypeptide comprising the amino acid sequence of SEQ ID NO: 1, the crystal having space group symmetry $C222_1$ and unit cell dimensions of a=75±5 Å, b=104±5 Å, c=100±5 Å, and $\alpha=\beta=\gamma=90°$, to one or more samples comprising a potential ligand of BACE; and
determining whether a ligand-BACE molecular complex is formed, wherein formation of a ligand-BACE molecular complex indicates the potential ligand has the ability to bind to BACE.

2. The method of claim 1 wherein the exposing comprises soaking.

3. The method of claim 1 wherein the one or more samples comprise a plurality of potential ligands.

4. A method of acquiring structural information for designing potential ligands for forming molecular complexes with BACE, the method comprising:
exposing a crystal of an unliganded BACE polypeptide comprising the amino acid sequence of SEQ ID NO: 1, the crystal having space group symmetry $C222_1$ and unit cell dimensions of a=75±5 Å, b=104±5 Å, c=100±5 Å, and $\alpha=\beta=\gamma=90°$, to a library of potential ligands having diverse shapes; and determining whether a ligand-BACE molecular complex is formed, wherein formation of a ligand-BACE molecular complex indicates a potential ligand has a structure that forms a molecular complex with BACE.

5. The method of claim 4 further comprising identifying the ligand that forms the ligand-BACE molecular complex.

6. The method of claim 5 wherein the determining and/or identifying comprises calculating an electron density function.

7. The method of claim 5 wherein the determining and/or identifying comprises collecting x-ray diffraction data.

8. The method of claim 1, wherein the crystal has a unit cell defined by the dimensions a, b and c, wherein a is 75 Å, b is 104 Å, c is 100 Å, and $\alpha=\beta=\gamma=90°$.

9. The method of claim 4, wherein the crystal has a unit cell defined by the dimensions a, b and c, wherein a is 75 Å, b is 104 Å, c is 100 Å, and $\alpha=\beta=\gamma=90°$.

* * * * *

SEQUENCE LISTING

```
<160> NUMBER OF SEQ ID NOS: 2

<210> SEQ ID NO 1
<211> LENGTH: 406
<212> TYPE: PRT
<213> ORGANISM: ARTIFICIAL
<220> FEATURE:
<223> OTHER INFORMATION: residues for the E. coli expressed recombinant
      human beta secretase

<400> SEQUENCE: 1

Met Arg Gly Ser Phe Val Glu Met Val Asp Asn Leu Arg Gly Lys Ser
1               5                   10                  15

Gly Gln Gly Tyr Tyr Val Glu Met Thr Val Gly Ser Pro Pro Gln Thr
            20                  25                  30

Leu Asn Ile Leu Val Asp Thr Gly Ser Ser Asn Phe Ala Val Gly Ala
        35                  40                  45

Ala Pro His Pro Phe Leu His Arg Tyr Tyr Gln Arg Gln Leu Ser Ser
    50                  55                  60

Thr Tyr Arg Asp Leu Arg Lys Gly Val Tyr Val Pro Tyr Thr Gln Gly
65                  70                  75                  80

Lys Trp Glu Gly Glu Leu Gly Thr Asp Leu Val Ser Ile Pro His Gly
                85                  90                  95

Pro Asn Val Thr Val Arg Ala Asn Ile Ala Ala Ile Thr Glu Ser Asp
            100                 105                 110

Lys Phe Phe Ile Asn Gly Ser Asn Trp Glu Gly Ile Leu Gly Leu Ala
        115                 120                 125

Tyr Ala Glu Ile Ala Arg Pro Asp Asp Ser Leu Glu Pro Phe Phe Asp
    130                 135                 140

Ser Leu Val Lys Gln Thr His Val Pro Asn Leu Phe Ser Leu Gln Leu
145                 150                 155                 160

Cys Gly Ala Gly Phe Pro Leu Asn Gln Ser Glu Val Leu Ala Ser Val
                165                 170                 175

Gly Gly Ser Met Ile Ile Gly Gly Ile Asp His Ser Leu Tyr Thr Gly
            180                 185                 190

Ser Leu Trp Tyr Thr Pro Ile Arg Arg Glu Trp Tyr Tyr Glu Val Ile
        195                 200                 205
```

```
-continued

Ile Val Arg Val Glu Ile Asn Gly Gln Asp Leu Lys Met Asp Cys Lys
    210                 215                 220

Glu Tyr Asn Tyr Asp Lys Ser Ile Val Asp Ser Gly Thr Thr Asn Leu
225                 230                 235                 240

Arg Leu Pro Lys Lys Val Phe Glu Ala Ala Val Lys Ser Ile Lys Ala
                245                 250                 255

Ala Ser Ser Thr Glu Lys Phe Pro Asp Gly Phe Trp Leu Gly Glu Gln
                260                 265                 270

Leu Val Cys Trp Gln Ala Gly Thr Thr Pro Trp Asn Ile Phe Pro Val
            275                 280                 285

Ile Ser Leu Tyr Leu Met Gly Glu Val Thr Asn Gln Ser Phe Arg Ile
    290                 295                 300

Thr Ile Leu Pro Gln Gln Tyr Leu Arg Pro Val Glu Asp Val Ala Thr
305                 310                 315                 320

Ser Gln Asp Asp Cys Tyr Lys Phe Ala Ile Ser Gln Ser Ser Thr Gly
                325                 330                 335

Thr Val Met Gly Ala Val Ile Met Glu Gly Phe Tyr Val Val Phe Asp
                340                 345                 350

Arg Ala Arg Lys Arg Ile Gly Phe Ala Val Ser Ala Cys His Val His
                355                 360                 365

Asp Glu Phe Arg Thr Ala Ala Val Glu Gly Pro Phe Val Thr Leu Asp
    370                 375                 380

Met Glu Asp Cys Gly Tyr Asn Ile Pro Gln Thr Asp Glu Ser Arg Ser
385                 390                 395                 400

His His His His His His
                405

<210> SEQ ID NO 2
<211> LENGTH: 13
<212> TYPE: PRT
<213> ORGANISM: ARTIFICIAL
<220> FEATURE:
<223> OTHER INFORMATION: synthetic peptide
<220> FEATURE:
<221> NAME/KEY: protein3
<222> LOCATION: (5)..(5)
<223> OTHER INFORMATION: statine
<220> FEATURE:
<221> NAME/KEY: misc_feature
<222> LOCATION: (5)..(5)
<223> OTHER INFORMATION: Xaa can be any naturally occurring amino acid

<400> SEQUENCE: 2

Ser Glu Val Asn Xaa Val Ala Glu Phe Arg Gly Gly Cys
1               5                   10
```